(12) United States Patent
Zelano et al.

(10) Patent No.: US 12,742,214 B2
(45) Date of Patent: Sep. 22, 2026

(54) DETERMINATION OF THE PRESENCE OF SARS-CoV-2 OR OTHER RESPIRATORY PATHOGEN IN A PERSON

(71) Applicant: NORTHWESTERN UNIVERSITY, Evanston, IL (US)

(72) Inventors: Christina Maria Zelano, Chicago, IL (US); Gregory Lane, Chicago, IL (US)

(73) Assignee: Northwestern University, Evanston, IL (US)

( * ) Notice: Subject to any disclaimer, the term of this patent is extended or adjusted under 35 U.S.C. 154(b) by 679 days.

(21) Appl. No.: 18/026,160

(22) PCT Filed: Sep. 16, 2021

(86) PCT No.: PCT/US2021/050569

§ 371 (c)(1),
(2) Date: Mar. 14, 2023

(87) PCT Pub. No.: WO2022/060917

PCT Pub. Date: Mar. 24, 2022

(65) Prior Publication Data

US 2023/0366041 A1 Nov. 16, 2023

Related U.S. Application Data

(60) Provisional application No. 63/079,254, filed on Sep. 16, 2020.

(51) Int. Cl.
*C12Q 1/70* (2006.01)
*A61B 5/097* (2006.01)
(Continued)

(52) U.S. Cl.
CPC .............. *C12Q 1/701* (2013.01); *A61B 5/097* (2013.01); *A61B 10/00* (2013.01); *C12Q 1/6851* (2013.01);
(Continued)

(58) Field of Classification Search
CPC ................................ A61B 5/097; A61B 10/00
See application file for complete search history.

(56) References Cited

U.S. PATENT DOCUMENTS 6,033,368 A * 3/2000 Gaston, IV ............ A61B 5/083 600/532
7,118,537 B2 10/2006 Baddour
(Continued)

FOREIGN PATENT DOCUMENTS

WO 2006136782 A1 12/2006
WO 2017153755 A1 9/2017

OTHER PUBLICATIONS

Khoubnasabjafari, M., et al., Apr. 2020, Exhaled breath condensate as a potential specimen for diagnosing COVID-19, Bioanalysis, 12(17):1195-1197, published online Apr. 15, 2020.*
(Continued)

*Primary Examiner* — Eric F Winakur
(74) *Attorney, Agent, or Firm* — Leydig, Voit & Mayer, Ltd.

(57) ABSTRACT

A method for measuring the presence of SARS-CoV-2 or other respiratory pathogen in a person comprises collecting a sample of condensed exhaled breath from the person and measuring the presence of SARS-CoV-2 or other respiratory pathogen in said sample, thus providing a method for determining whether a person is capable of transmitting SARS-CoV-2 or other respiratory pathogen to other persons.

8 Claims, 17 Drawing Sheets

(51) Int. Cl.
*A61B 10/00* (2006.01)
*C12Q 1/6851* (2018.01)
*G01N 1/42* (2006.01)

(52) U.S. Cl.
CPC ........ *G01N 1/42* (2013.01); *A61B 2010/0087* (2013.01)

(56) References Cited

U.S. PATENT DOCUMENTS

| | | | | |
|---|---|---|---|---|
| 7,547,285 | B2 * | 6/2009 | Kline | A61B 5/097 600/529 |
| 8,491,494 | B2 * | 7/2013 | Kline | A61B 5/097 600/529 |
| 2004/0138577 | A1 | 7/2004 | Kline | |

OTHER PUBLICATIONS

Korean Intellectual Property Office (ISR/KR), "International Search Report for PCT/US2021/050569", Korea, Jan. 6, 2022.

Khoubnasabjafari, M. et al., 'Exhaled breath condensate as a potential specimen for diagnosing COVID-19', Bioanalysis, Apr. 15, 2020, internal pp. 1-3.

Zheng, Y. et al., 'Bacterial pathogens were detected from human exhaled breath using a novel protocol', Journal of aerosol science, 2018, pp. 224-234.

* cited by examiner

Exhaled Breath Condensate Collection

Step 1. Insert mouthpiece and put on cooling sleeve.

Step 2. Breathe through tube for 5 minutes.

Step 3. Remove mouthpiece and cooling sleeve, insert plunger.

Exhaled Breath Condensate Collection

DETERMINATION OF THE PRESENCE OF SARS-CoV-2 OR OTHER RESPIRATORY PATHOGEN IN A PERSON

CROSS-REFERENCE TO RELATED PATENT APPLICATION

This application claims priority to and the benefit of U.S. Provisional Patent Application Ser. No. 63/079,254, filed Sep. 16, 2020, which is incorporated herein in its entirety by reference.

FIELD OF THE INVENTION

The present invention relates to a method for determination and quantitation of the presence of SARS-CoV-2 and/or other respiratory pathogens in a human by analysis of exhaled breath condensate. The present invention also relates to an apparatus for collection of a human exhaled breath condensate for the purpose of determination and quantitation of the presence of SARS-CoV-2 and/or other respiratory pathogens.

BACKGROUND OF THE INVENTION

This invention relates to detection of respiratory pathogens.

SUMMARY OF THE INVENTION

SARS-CoV-2 spreads through exhaled respiratory droplets and aerosols, causing the disease COVID-19 (the term "SARS-CoV-2" refers to the virus and the term "COVID-19" refers to the disease caused by the virus, though the two terms are sometimes used interchangeably). Understanding transmission of SARS-CoV-2 requires direct measurement of SARS-CoV-2 viral loads in exhaled breath of a human in order to gain insight on such metrics as how exhaled viral loads vary across individuals, how exhaled viral loads vary over the course of infection, how exhaled viral loads relate to symptoms and symptom onset, and other metrics of exhaled viral load.

Rather than relying on viral loads obtained from inside the nasal cavities or other internal sites, which provide direct measures of internal viral loads but indirect measures of infectiousness, direct quantification of SARS-CoV-2 in breath provides direct knowledge of how much virus an individual is currently exhaling into their environment, and thereby exposing others, and is therefore a direct measure of infectiousness.

Medical professionals currently do not have an understanding of how individual variation in infectiousness contribute to the spread of COVID-19. Obtaining this information at the individual level would improve the accuracy of quarantine durations, and allow for individualized quarantine schedules, and optimal minimization of transmission of the virus. For example, it is possible that certain infected individuals continue to exhale virus into the environment after symptoms have abated, or for longer than expected durations following infection onset (>10 days). It is also possible that certain infected individuals continue to show the presence of the virus at internal swab sites such as the nasopharynx while no longer shedding the virus on their breath, and thus can test positive with swab-based testing even though they are no longer infectious. It is also possible that some individuals shed unusually high levels of virus during infection, while others may shed unusually low levels. This important information cannot be obtained without directly measuring and characterizing levels of SARS-CoV-2 viral load in exhaled breath. Therefore, an accurate, portable, inexpensive device that allows patients to self-collect breath samples at their own homes holds potential to improve global efforts to reduce transmission of COVID-19.

In general, the present invention has developed a self-administered test kit, including an Exhaled Breath Collection (EBC) device, to obtain exhaled breath samples for the purpose of measuring SARS-CoV-2 or other respiratory pathogens, which is an inexpensive, portable, easy-to-use device that can be used by patients themselves to collect exhaled breath samples within their own homes. The invention can also easily be used in the clinic.

Furthermore, the present invention also provides a method for determination and quantitation of the presence of SARS-CoV-2 and/or other respiratory pathogens in a human by analysis of exhaled breath condensate.

This invention has been used to collect and analyze over 200 samples from COVID-19 tested patients who were treated at Northwestern Memorial Hospital Emergency Department or Immediate Care Clinics. This analysis has shown that this invention has a high accuracy and sensitivity.

The present invention was able to determine the number of virions each patient was exhaling per minute during their breath collection session, including, for some patients, two sessions each day over the course of their infection. The present invention also shows the relationships between symptom severity, symptom type, days since symptom onset, and levels of exhaled virus. The results show that this invention is accurate, easy for patients to use, and can provide a reliable measure of how much virus a patient is exhaling into the environment.

This device will be useful not only for individuals who want to know their infectiousness status, but also for researchers who want to develop a better understanding of transmission of SARS-CoV-2 via breath. This invention provides an accurate and inexpensive tool that researchers can use to quickly obtain large amounts of exhaled breath data from COVID-19 patients.

According to a first aspect of the invention, there is provided a method for determining the presence of SARS-CoV-2 or other respiratory pathogen in a person, the method comprising the steps of collecting a sample of condensed exhaled breath from the person; and detecting the presence of SARS-CoV-2 or other respiratory pathogen in the sample.

According to another aspect of the invention, there is provided a method for determining the presence of SARS-CoV-2 or other respiratory pathogen in a person, in which the condensed exhaled breath is substantially only orally exhaled, substantially only nasally exhaled, or orally and nasally exhaled.

According to another aspect of the invention, there is provided a method for determining the presence of SARS-CoV-2 or other respiratory pathogen in a person, in which the detection is performed by PCR, preferably by quantitative PCR, more preferably by real-time reverse transcriptase quantitative PCR, or by reverse transcriptase droplet digital PCR.

According to another aspect of the invention, there is provided a method for determining the presence of SARS-CoV-2 or other respiratory pathogen in a person, in which the detection is performed by culturing the virus using any culturing method, preferably plaque assay, or immunohistochemistry.

According to another aspect of the invention, there is provided a method for determining whether a first person is capable of transmitting SARS-CoV-2 or other respiratory pathogen to a second person, the method comprising steps of collecting a sample of condensed exhaled breath from the first person; quantitating the amount of SARS-CoV-2 or other respiratory pathogen in the sample; and assessing whether the amount is sufficient to infect, and the extent to which the amount is sufficient to infect, a second person.

According to another aspect of the invention, there is provided a method for determining whether a first person is capable of transmitting SARS-CoV-2 or other respiratory pathogen to a second person, in which the assessing includes comparing the amount of SARS-CoV-2 or other respiratory pathogen in the sample to a known infectious dose of SARS-CoV-2 or other respiratory pathogen.

According to another aspect of the invention, there is provided a method for determining whether a first person is capable of transmitting SARS-CoV-2 or other respiratory pathogen to a second person, in which the collecting, quantitating and assessing steps are repeated in order to monitor the infectiousness of said person and/or to assess when the first person is no longer infectious.

According to another aspect of the invention, the condensed exhaled breath sample is collected in a chilled tube.

According to another aspect of the invention, the condensed exhaled breath sample is collected in a chilled tube; the tube being constructed of two walls with a space between such that a cavity is formed around the tube and the cavity is filled with water or a gel or another substance, typically reusable, which retains a low temperature after being placed in the freezer or refrigerator for a period of time.

According to another aspect of the invention, a device for collecting exhaled breath condensate of a subject, comprising a sample tube having a first end receiving exhaled breath and a second end from which exhaled breath exits; a cooling sleeve for cooling the sample tube; and a mouthpiece or nose mask adapted to communicate with the first end of the sample tube for directing exhaled breath into the sample tube.

According to another aspect of the invention, a device for collecting exhaled breath condensate of a subject, in which the mouthpiece or the nose mask are arranged in a straight line with respect to the sample tube in order to produce breath flow into the tube which avoids an angular path.

According to another aspect of the invention, a device for collecting exhaled breath condensate of a subject, in which the second end of the sample tube has an aperture whose diameter is narrower than the diameter of the sample tube so as to create resistance to exhaled breath flowing in the sample tube.

According to another aspect of the invention, a device for collecting exhaled breath condensate of a subject, in which the diameter of the aperture is about ¼ of the diameter of the sample tube.

According to another aspect of the invention, a device for collecting exhaled breath condensate of a subject, in which the device further comprising a one-way valve placed between the mouthpiece or the nose mask and the sample tube.

According to another aspect of the invention, a device for collecting exhaled breath condensate of a subject, in which the device further comprising a plunger to be inserted into the sample tube via the first end of the sample tube. The plunger and the sample tube form an airtight connection such that then the plunger is pushed into the sample tube, the exhaled breath condensate inside the sample tube would be removed from the sample tube via the second end of the sample tube.

According to another aspect of the invention, a device for collecting exhaled breath condensate of a subject, in which the device further comprising an insulator placed outside of the cooling sleeve so as to thermally insulate the cooling sleeve from surrounding environment.

According to another aspect of the invention, a kit suitable for use in carrying out the methods of this invention comprising the components for assembling the aforementioned device, a vial for receiving the exhaled breath condensate when the exhaled breath condensate exits the second end of the sample tube; and a cap for the vial.

According to another aspect of the invention, the pathogen is SARS-CoV-2 or other respiratory pathogens.

In all the foregoing aspects, this invention is preferably applied to viral pathogens, particularly preferably coronaviruses, e.g., SARS-CoV-1, most preferably SARS-CoV-2, or influenza viruses, and also applied to bacterial pathogens, such as *Mycobacterium tuberculosis, Streptococcus pneumonia*, etc., and also applied to fungal pathogens.

These and other aspects of the present invention will become apparent from the following description of the preferred embodiments, taken in conjunction with the following drawings, although variations and modifications therein may be affected without departing from the spirit and scope of the novel concepts of the disclosure.

BRIEF DESCRIPTION OF THE DRAWINGS

The accompanying drawings illustrate one or more embodiments of the invention and, together with the written description, serve to explain the principles of the invention. The same reference numbers may be used throughout the drawings to refer to the same or like elements in the embodiments.

DETAILED DESCRIPTION OF THE INVENTION

Figure 1A:
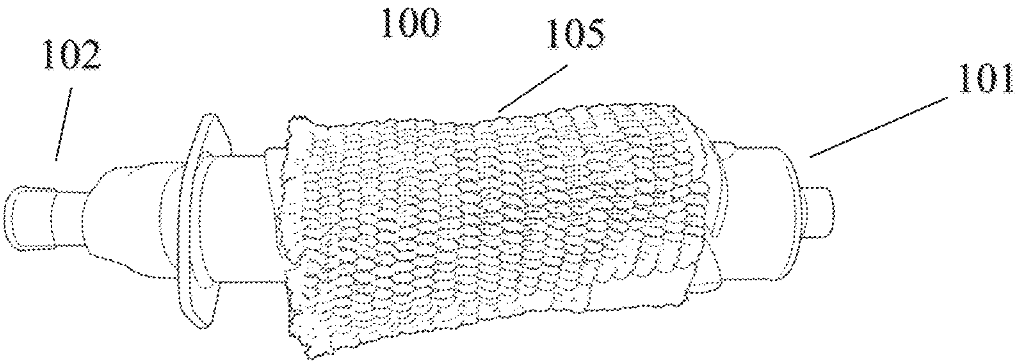
FIG. 1A illustrates a diagram of this invention assembled.

The invention will now be described more fully hereinafter with reference to the accompanying drawings, in which exemplary embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Like reference numerals refer to like elements throughout.

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and in no way limits the scope and meaning of the invention or of any exemplified term. Likewise, the invention is not limited to various embodiments given in this specification.

It will be understood that, as used in the description herein and throughout the claims that follow, the meaning of "a", "an", and "the" includes plural reference unless the context clearly dictates otherwise. Also, it will be understood that when an element is referred to as being "on" another element, it can be directly on the other element or intervening elements may be present therebetween. In contrast, when an element is referred to as being "directly on" another element, there are no intervening elements present. As used herein, the term "and/or" includes any and all combinations of one or more of the associated listed items.

It will be understood that, although the terms first, second, third etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below could be termed a second element, component, region, layer or section without departing from the teachings of the invention.

Furthermore, relative terms, such as "lower" or "bottom" and "upper" or "top," may be used herein to describe one element's relationship to another element as illustrated in the Figures. It will be understood that relative terms are intended to encompass different orientations of the device in addition to the orientation depicted in the Figures. For example, if the device in one of the figures is turned over, elements described as being on the "lower" side of other elements would then be oriented on "upper" sides of the other elements. The exemplary term "lower", can therefore, encompasses both an orientation of "lower" and "upper," depending of the particular orientation of the figure. Similarly, if the device in one of the figures is turned over, elements described as "below" or "beneath" other elements would then be oriented "above" the other elements. The exemplary terms "below" or "beneath" can, therefore, encompass both an orientation of above and below.

It will be further understood that the terms "comprises" and/or "comprising," or "includes" and/or "including" or "has" and/or "having", or "carry" and/or "carrying," or "contain" and/or "containing," or "involve" and/or "involving, and the like are to be open-ended, i.e., to mean including but not limited to. When used in this disclosure, they specify the presence of stated features, regions, integers, steps, operations, elements, and/or components, but do not preclude the presence or addition of one or more other features, regions, integers, steps, operations, elements, components, and/or groups thereof.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

As used in this disclosure, "around", "about", "approximately" or "substantially" shall generally mean within 20 percent, preferably within 10 percent, and more preferably within 5 percent of a given value or range. Numerical quantities given herein are approximate, meaning that the term "around", "about", "approximately" or "substantially" can be inferred if not expressly stated.

As used in this disclosure, the phrase "at least one of A, B, and C" should be construed to mean a logical (A or B or C), using a non-exclusive logical OR. As used herein, the term "and/or" includes any and all combinations of one or more of the associated listed items.

Embodiments of the invention are illustrated in detail hereinafter with reference to accompanying drawings. The description below is merely illustrative in nature and is in no way intended to limit the invention, its application, or uses. The broad teachings of the invention can be implemented in a variety of forms. Therefore, while this invention includes particular examples, the true scope of the invention should not be so limited since other modifications will become apparent upon a study of the drawings, the specification, and the following claims. For purposes of clarity, the same reference numbers will be used in the drawings to identify similar elements. It should be understood that one or more steps within a method may be executed in different order (or concurrently) without altering the principles of the invention.

In accordance with this invention, exhaled breath is condensed and collected into a liquid sample that can then be analyzed for the presence and quantity of SARS-CoV-2 virus or other respiratory pathogen. Previous research suggests viruses are present at a fairly low rate in exhaled breath condensate from known infected patients (8 to 20% of patients). This invention finds much higher rates with the disclosed method (e.g., 90%)

A preferred device for use in this invention is disclosed herein. Its use is described in detail below in conjunction with the figures. Analysis methods per se for determining the levels of virus present in samples are conventional and include PCR, preferably quantitative PCR, more preferably real-time reverse transcriptase quantitative PCR, and/or reverse transcriptase droplet digital PCR.

Because of the advantages afforded by the method of this invention and the fact that exhaled breath is its source of viral content, in a preferred aspect, this invention can be used to determine the infectiousness of a person with respect to SARS-CoV-2 or other respiratory pathogen.

By collecting a patient's exhaled breath and measuring SARS-CoV-2 or other respiratory pathogen within it, it can be determined whether an individual is shedding the virus into the environment through exhalation. By using this invention, it has been discovered that some patients who are tested positive for COVID-19 (the disease caused by the SARS-CoV-2 virus) via conventional nasopharyngeal swab do not have detectable levels of SARS-CoV-2 in their exhalates. In contrast, some other positive patients have large amounts of SARS-CoV-2. It is therefore very useful to determine whether or not a patient is exhaling virus, and if so, to what extent. Data collected by the present invention suggest there are variable levels of virus in exhaled breath samples, ranging from undetected to CT values of 27 and lower. (CT (cycle threshold) value is the common parameter for presenting PCR results; the lower the value, the higher the content of the virus.)

One of skill in the art can routinely determine a suitable method for setting a threshold for infectiousness. For example, in one technique, SARS-CoV-2 virus samples, freely provided to research labs, can be used to conduct a standard curve analysis using rRT-qPCR with TaqMan probes. The standard curve analysis will determine the relationship between CT values and the number of viral particles present in a sample, thus allowing absolute quantification of viral particles in a sample. In another technique, by performing ddPCR analysis on a sample, one can determine absolute quantification of viral particles as a direct output of the analysis. Optionally, by combining absolute quantification with a plaque assay of the exhaled breath condensate sample type (which will determine the presence and/or percentage of infectious virus present in a typical sample), one can accurately estimate the amount of infectious virus present in any particular sample and compare that amount to the known infectious dose of the virus in order to determine the infectiousness of an individual at the time of the test. (Mendoza, E. J., Manguiat, K., Wood, H., & Drebot, M. (2020). Two detailed plaque assay protocols for the quantification of infectious SARS-CoV-2: (Current Protocols in Microbiology, 57, e105. doi: 10.1002/cpmc.105)

Current research suggests one measure of infectious dose (ID50) for SARS-CoV-2 is 280 viral particles or even lower, and that SARS-CoV-2 can be detected in aerosols for up to 3 hours. (Karimzadeh et al, Epidemiology & Infection, Vol 149, 2021, e96; Watanabe T.; Bartrand T. A.; Weir M. H.; Omura T.; Haas C. N. Development of a Dose-Response Model for SARS Coronavirus. Risk Anal. 2010, 30 (7), 1129-1138). Accordingly, using the method of this invention (with its timed, e.g., 10-minute, exhaled breath collection period), an individual who is shedding more than, e.g., 280/18 (infectious dose divided by the number of ten-minute intervals occurring in a 3 hour window) viral particles in a ten minute time frame would be considered to be infectious. This is one example of "standard conditions" used to determine the infectiousness of a person. Of course, other sets of standard conditions can also reasonably be used in conjunction with this invention, as will be evident to those skilled in viral infectiousness in consideration of applicable factors, such as local environments, patient conditions, etc. Under the chosen standard conditions, it can straightforwardly be determined whether an individual patient is infectious or not by, e.g., collecting exhaled breath condensate (EBC) for a 10 minute duration, performing PCR (rRT-qPCR or ddPCR) to determine the corresponding CT level and referring to a corresponding standard curve analysis to determine absolute quantification, as discussed above, or in the case of ddPCR, absolute quantification is directly obtained.

Using this method of the present invention, it can also be determined, not only whether a patient is infectious, but also how infectious the patient is. A patient who is shedding infectious virions or other respiratory pathogens on exhaled breath equivalent to the ID50 would be considered infectious at the minimal level. And patients shedding higher levels of virus would be proportionately more infectious. Patients could then be categorized more finely according to measured infectiousness level, rather than as simply positive and thus contagious or simply negative and thus likely not contagious.

Further, this method can be used to determine how many infectious virions a patient is exhaling per amount of time, e.g. per minute. Such information could be used to assess the risk of exposure over time to a patient, by, for example, clinical staff, and could be used to limit exposure to infectious patients to an amount of time corresponding to less than an infectious dose. Continual monitoring of patients using this invention can determine how infectiousness varies for a given individual and/or on average over the course of an infection. Such information could be used to guide public health decisions such as quarantine durations and provide guidance on social, work, family, and other interactions. This information would thus have a profound impact on quality of life of infected individuals and on economic productivity of an individual and of a community as a whole.

Furthermore, as discussed below, the kit of this invention can be taken home and re-used by the same individual. Accordingly, patients who tested positive for COVID-19 and are self-isolating at home can produce one or two or more samples per day from home, send them to a lab for analysis, and determine at what time point in the course of their disease they stopped shedding virus on their breath (stopped being contagious). This can contribute very useful information to guide decisions on duration of quarantine and the like.

As for the device and kit of this invention, they are simple and inexpensive. The device is made from commonly available parts, is fully washable and re-usable, and is easy to manufacture. Data from patients who have reused the device multiple times per day over weeks during their illnesses, have been able to plot the change in their exhaled viral load over days of illness. This represents a major advantage for patient management.

Particular preferred features of the device include its straight design whereby it directs exhaled breath straight into the tube, avoiding angles which can compromise sample quality and volume; its full portability from assembly to completed sample in the vial ready for analysis; its reusability by the same user; its ease and intuitiveness of use whereby it can be used in a residential or otherwise non-clinical setting by a lay user following simple pictographic instructions, as exemplified in the drawings; its low cost based on its easy-to-find disposable parts which do not require complex matching or specialized manufacture; its use of off-the-shelf cooling sleeves, mouthpieces and one-way valves; its disposability, including the plunger, and its lack of specially manufactured parts requiring retention, recovery or sterilization, etc. When the collection and testing are accomplished, the entire device can simply be trashed.

A further advantageous feature is the narrowness of the exit end of the tube into which breath is exhaled (non-mouthpiece end). The exit end aperture diameter should be about ¼ of the diameter of the body of the tube. In one embodiment, this end can routinely be modified from the manufactured size of a typical syringe (e.g., Monoject 50/60 mL catheter tip needless) to be about ¼", or ¼ of the diameter of the tube. This creates resistance to exhalation through the tube, which improves quality (e.g., amount of RNA or other measurable) and volume of sample.

These features distinguish from prior art alternatives such as the RTube which, for example, lacks full portability in view of the nature of its cooling sleeve and plunger. In contrast to the present invention, cooling sleeves of the prior art are metallic, and thus not a flexible, inexpensive material, and the plungers of the prior art are metallic, thus not portable or disposable, thus the RTube is not designed for immediate plunging and is large and heavy. In lacking a design for immediate plunging, the device of prior art is not suited to immediately recover the condensate sample into a vial, thus preventing some advantages offered by immediate plunging, for example: immediate denaturing of an infectious sample by adding the sample to a vial containing a lysing solution; immediate stabilization of a sample by adding the sample to a vial containing a stabilizing solution such as viral transport medium; ease of immediate storage of a sample refrigeration or freezing of the same is required; ease of mailing a sample by mailing a small vial. Furthermore, the pathway through which the exhaled breath passes in the device of prior art is not direct as that for the present invention, hence, the sample volume and quality of prior art is compromised as a result. Similarly, the exit aperture in the device of prior art is the same as its tube diameter, and thus sample volume and quality is compromised as well.

FIGS. 1A/1B-5 and 14A/B show embodiments of this invention for EBC device as described herein.

Typical prior art EBC devices are bulky, non-portable machines. Portable options exist, but are typically expensive, overly complex and require additional equipment for sample recovery, which must be performed in the lab.

In contrast to prior art, as reflected in FIG. 1A, the present invention has developed a streamlined, portable, easy-to-use EBC collection device, this is, this invention 100, for collection of EBC from patients, such as COVID-19 patients. Patients breathe into the syringe tube 101 through the mouthpiece 102 (left side of the tube in FIG. 1A). The cooling sleeve 105 (covered by white protective fabric in the photo) causes warm exhaled air to condense inside the syringe tube 101.

Figures 6A, 6B:
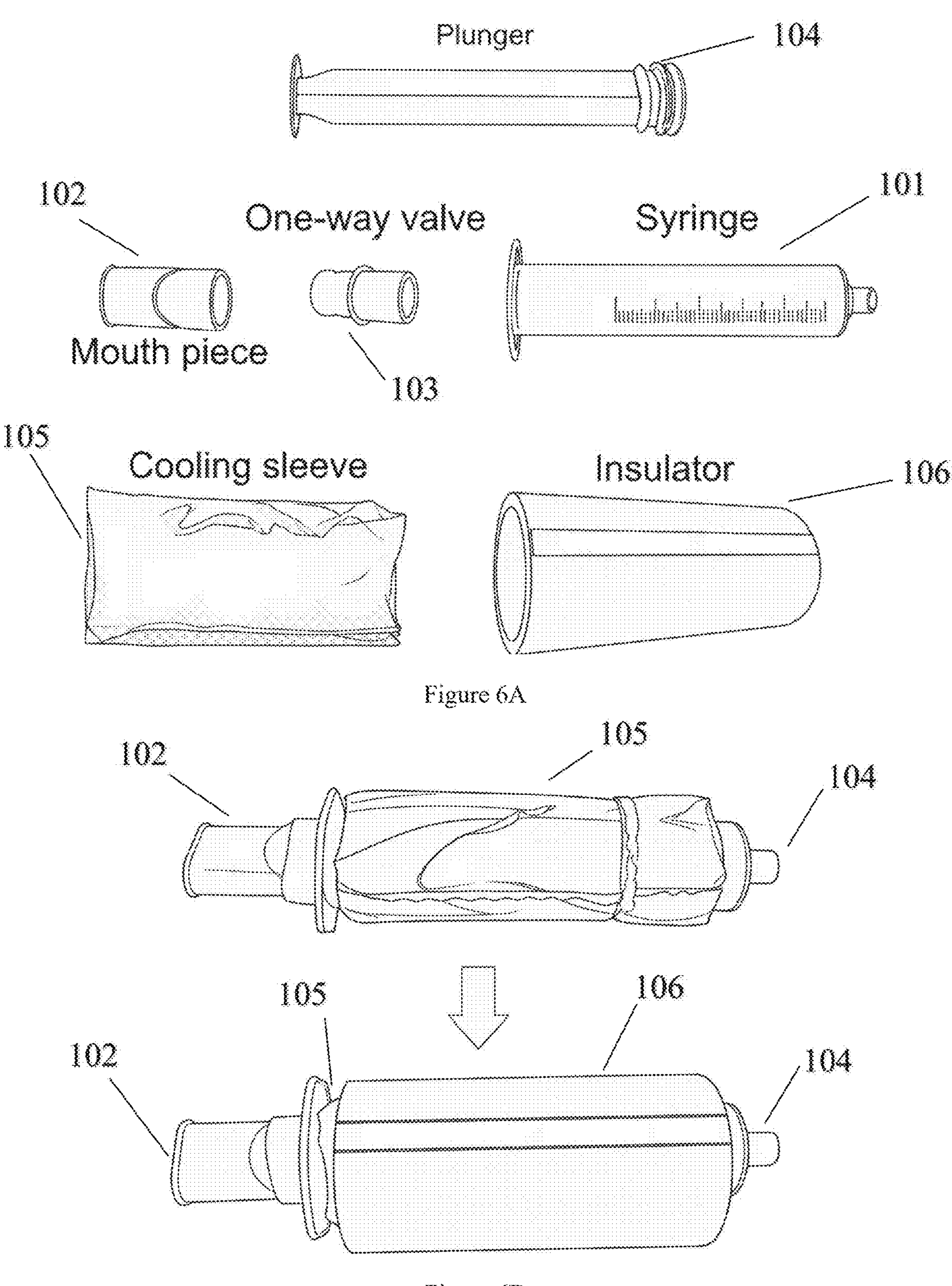
FIG. 6A illustrates an exploded view of this invention with a cooling sleeve and an insulator.
FIG. 6B illustrates an assembled view of this invention with a cooling sleeve and an insulator.

In another embodiment of the present invention, as reflected in FIG. 6A, this invention 100 used for EBC collection may comprise a syringe tube 101 for fluidly receiving the exhaled breath from a mouth piece 102 and condensing the exhaled breath into droplets; a mouth piece 102 fluidly connected to the syringe 101 on one end, for receiving the exhale breath from a human's mouth or nose via the other end; a one-way valve 103 placed in between and the mouth piece 102 and syringe tube 101 to prevent the back flow of the exhaled breath entered into the syringe 101; a cooling sleeve 105 wrapping around the outer surface of syringe 101 for decreasing the temperature of the exhaled breath so as to accelerate the condensation process; an insulator 106 to thermally contain the cooling sleeve; and a plunger 104 to be received by the the syringe 101 and form an-air-tight connection, so as to remove the exhaled breath condensate from the syringe 101 into a viral tube.

FIG. 6B illustrates one embodiment in which the cooling sleeve 105 wraps around the outer surface of the syringe 101 before the insulator 106 is placed to contain the cooling sleeve 105 inside the insulator 106.

Figure 14A:
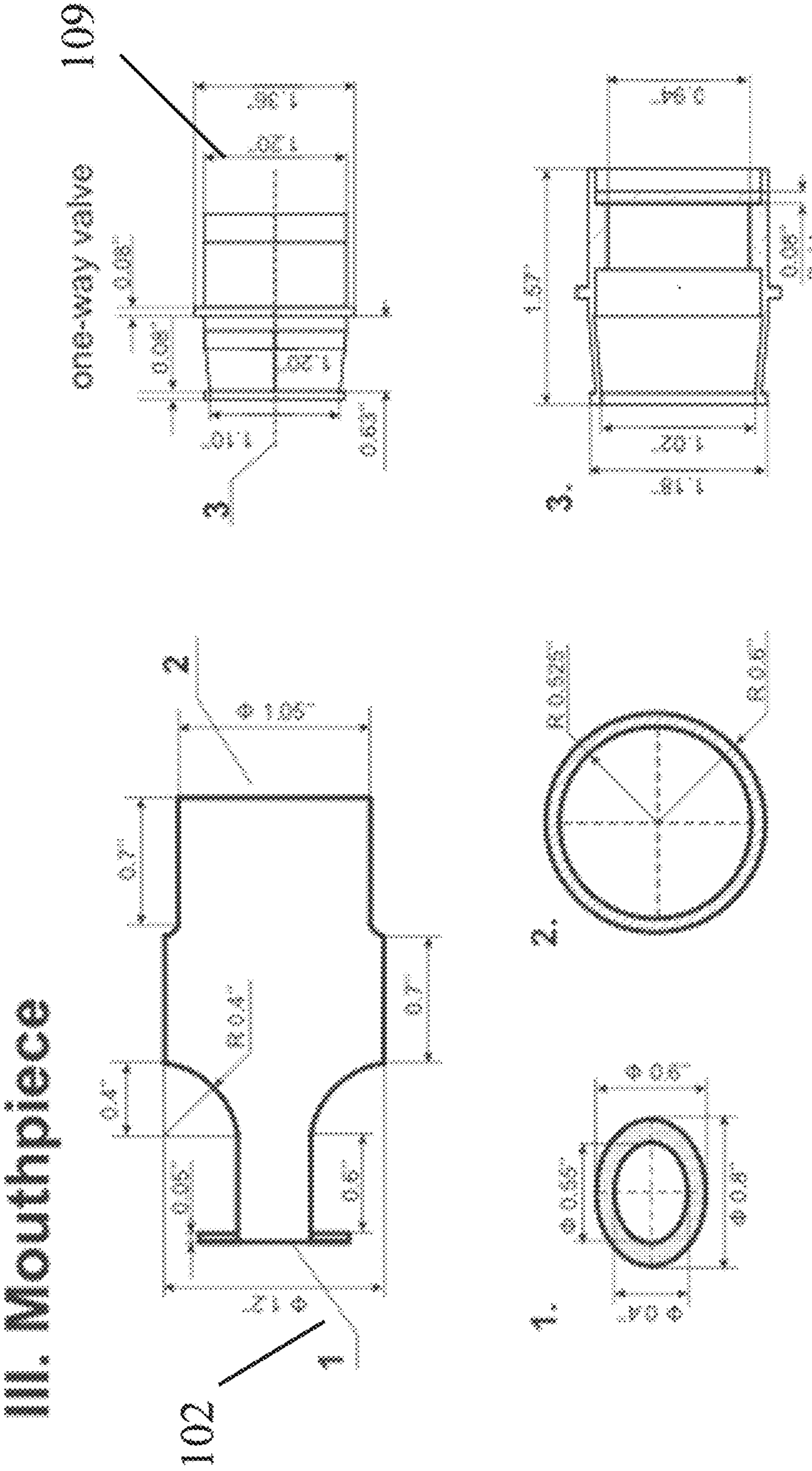
FIG. 14A-B illustrate a mouth piece with one-way valve, e.g. a flutter valve, of this invention and a nasal piece with one-way valve, e.g. a flutter valve, of this invention.
Figure 14B:
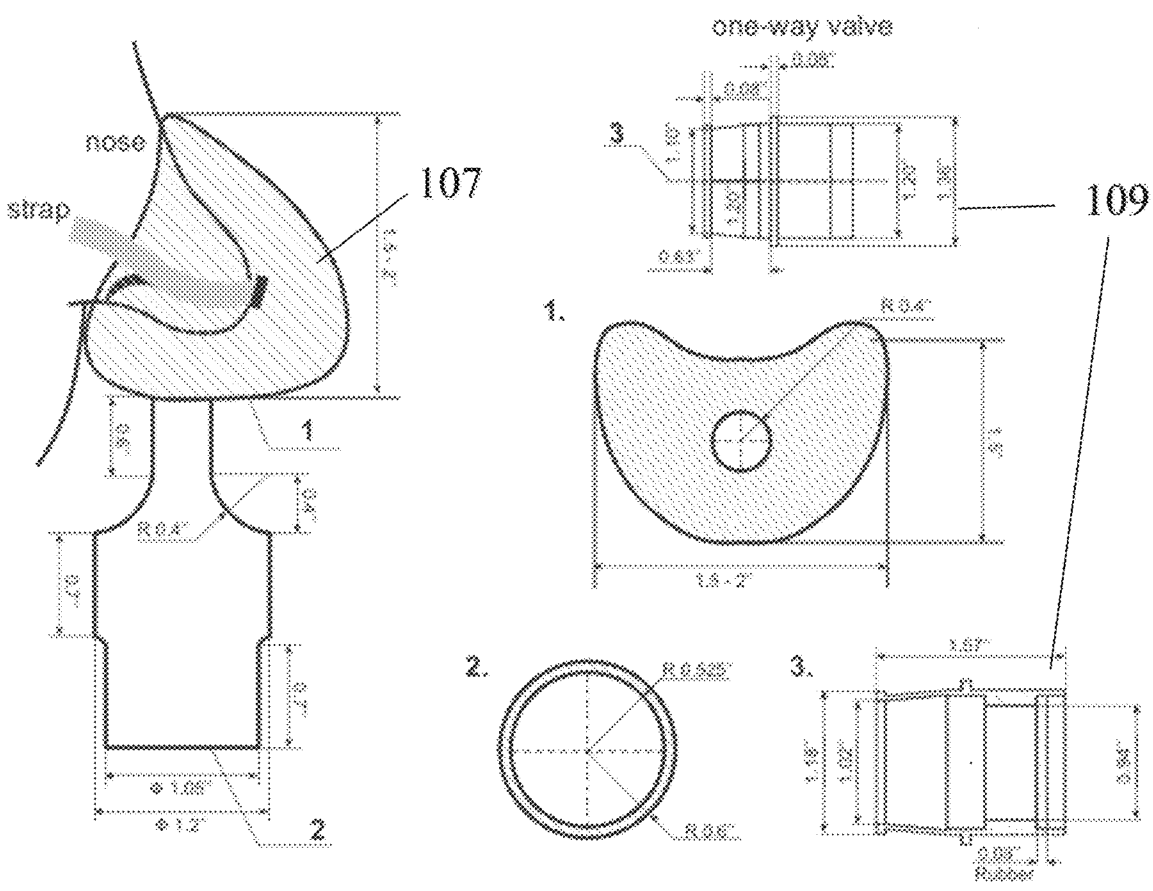

FIG. 14A-B illustrate one embodiment in which the one-way valve 109 is a flutter-type valve.

In one embodiment, this invention 100 can be prepared by placing a mouthpiece 102 (e.g., polyethylene or other food-grade plastic, e.g. the Vyaire Medical SpiroSoft mouthpiece part #2014846-006, or e.g. Vyaire Medical Nebulizer mouthpiece part #132410) with a one-way valve 103/109 (e.g., duckbill style, or plastic flutter valve) into the large open end of the syringe tube 101 of collecting oral EBC; or placing a nasal mask 107 with a one-way valve 103/109 (e.g., silicone, duckbill style, or flutter valve style) into the large open end of the syringe tube 101 if collecting nasal EBC; or by placing a face mask (covering both nose and mouth) with a one-way valve 103/109 (e.g., silicone, duck-bill style, or flutter-style valve, e.g. the Vyaire Medical one-way valve part #001800) into the large open end of the syringe tube 101 if collecting combined oral and nasal EBC.

The joint between the inner wall of the syringe tube 101 and the outer wall of the mouthpiece 102/nasal mask 107/facemask forms an airtight seal, either with a silicon ring or by exact fit. A cooling sleeve 105 which has been cooled, e.g., in a −20° C. freezer for at least two hours is placed around the tube of the syringe in order to cool the tube. In one embodiment, the cooling sleeve 105 is a Torex hot/cold therapy finger size sleeve (about 4" long, 1" inner diameter) or any cooling sleeve that is made with a flexible plastic shell and filled with a suitable gel cold pack material which can maintain −20° C. temperature for ten minutes while sitting at room temperature after two hours in a −20° C. freezer.

Preferably, an insulator 106 (e.g., Surgilast tubular elastic bandage retainer, size 6) is placed over the cooling sleeve in order to protect the user's fingers from the cold of the cooling sleeve during use.

Figure 1B:
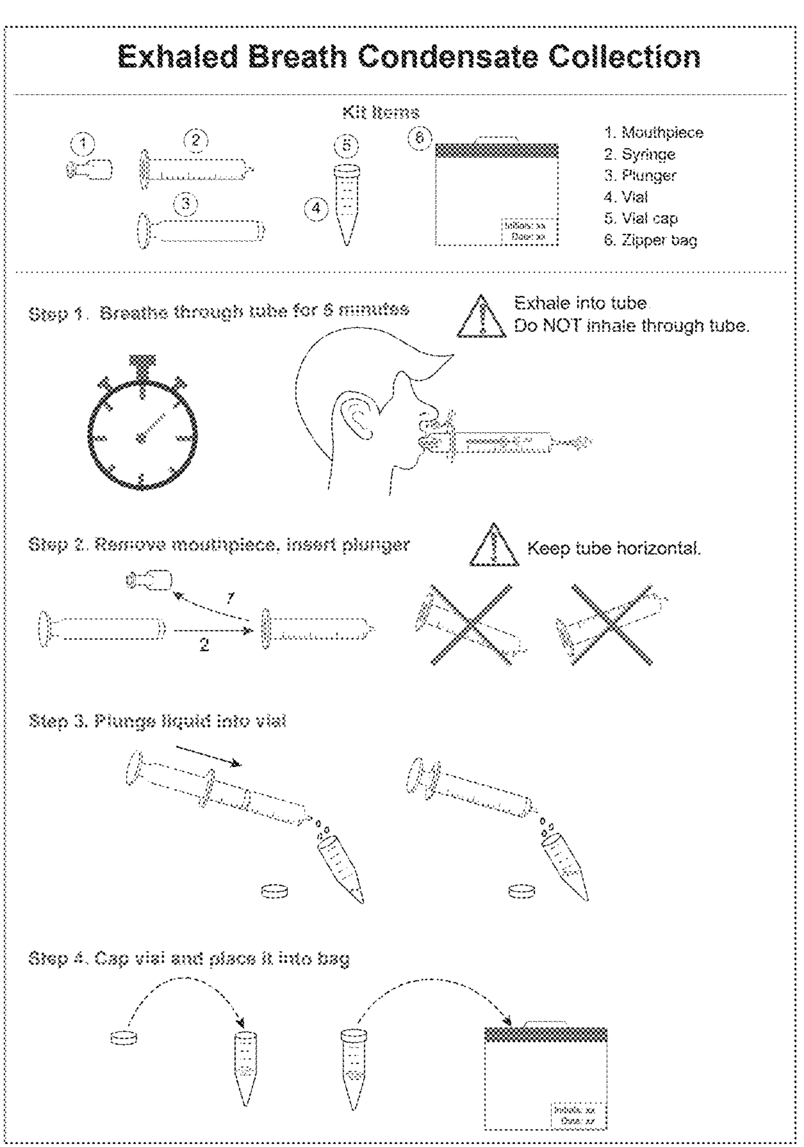
FIG. 1B illustrates written instructions provided with this invention.

As reflected in FIG. 1B, the collection protocol involves simple, easy to follow steps, resulting in a ready-to-analyze sample. The instructions provided to patients are shown in FIG. 1B; producing a sample involves only 4 easy steps.

In particular, during the step 1, a patient simply breathes naturally into the syringe tube 101 via the mouth piece 102 or a nasal mask 107 for 5-10 minutes, during which the patient can watch tv or read. During the breath session, this invention 100 works by cooling the wall of the syringe tube 101 so that exhaled breath condenses onto the inner wall of the syringe tube 101. A typical 10-minute breathing session yields around 1 mL of liquid sample. In one embodiment, the cooling process can be performed at a regular room temperature. In another embodiment, the cooling sleeve 105 can be used to wrap around the outer surface of the syringe tube 101 so as to reduce the temperature and therefore accelerate the condensation process. In another embodiment, an insulator 106 can be used to contain the cooling sleeve 105 inside the insulator 106, so as to thermally insulate the cooling sleeve 105 from the surrounding environment.

In one embodiment of the present invention, the method may include placing a nasal mask over the patient's nose, having the patient breathing into it through his or her nose for ten minutes, in deep naturally-paced breaths. The nasal mask 107 may be connected to a plastic tube, which may be cooled by one or a series of freezer-pack-type sleeves. As the patient's breath moves through the tube 101, it naturally condenses on the cooled inside surface of the tube. After the ten-minute breathing session, the patient may pour the liquid condensate into a collection vial which contains a stabilizing transport medium. The sanitized sample is then sent by mail to a lab for analysis for the presence of SARS-CoV-2 or other respiratory pathogen.

In yet another embodiment of the invention, the method may include collecting an oral breath sample as well, and comparing virus levels and optionally other biomarkers present in nasal versus oral samples.

In yet another embodiment of the invention, the method may include collecting a breath sample, either oral or nasal or both, and comparing the results to a swab sample, e.g., a nasal or oral swab sample, a nasopharyngeal swab sample, an oralpharyngeal swab sample, or any other swab sample which determines the presence of a virus or other pathogen in a person. The purpose of this comparison is to determine whether the virus or other pathogen is on the exhaled breath of a person regardless of whether the virus or other pathogen is in a person.

In yet another embodiment of the invention, the method may include collecting a breath sample, either oral or nasal or both, in order to determine whether the virus or other respiratory pathogen is in the exhaled breath of a person.

During the step 2, the patient detaches the mouth piece 102 from the syringe tube 101 and insert the plunger 104 into the syringe tube 101 so as to form an airtight connection. It should be noted that, during the process, the syringe tube 101 should remain roughly horizontal, so as to ensure the condensate remains inside the syringe tube 101.

During the step 3, the plunger 104 is pushed by the patient into the interior space of the syringe tube 101, and the air-tight connection between the plunger 104 and syringe tube 101 would facilitate the removing of the exhaled breath condensate from interior space of the syringe tube 101 to enter into a vial tube via a small opening end of the syringe tube 101.

After the condensate is removed to the viral tube, the vial tube is capped and moved to a mail package in step 4, so as to sending the collect condensate sample to a laboratory for further analysis.

Figure 6C:
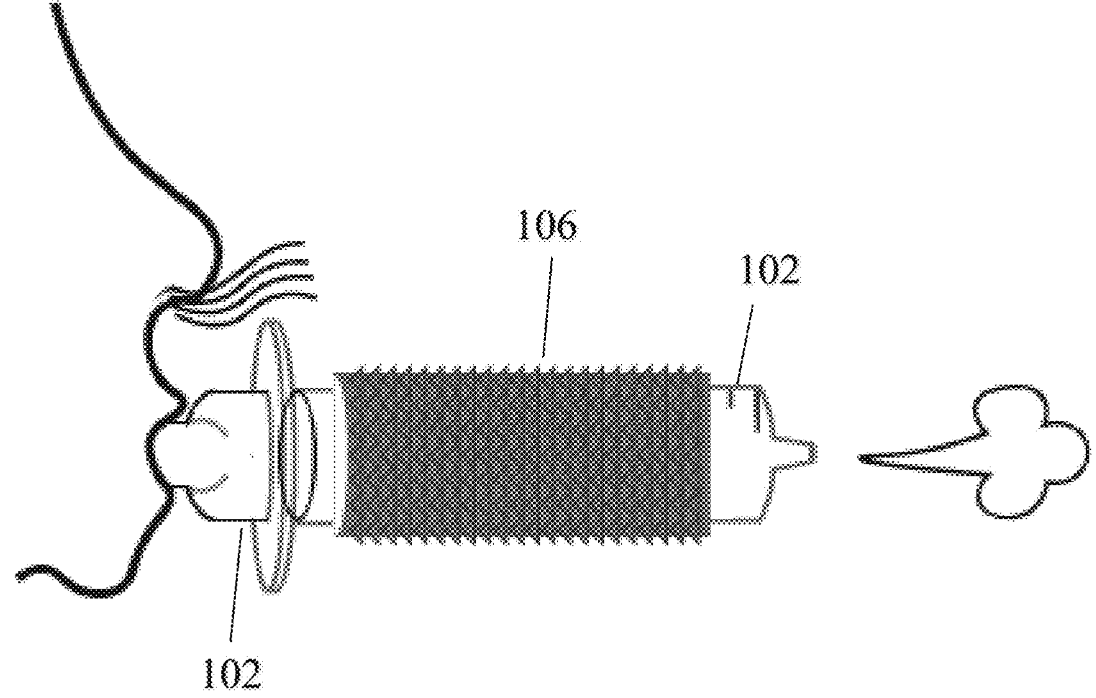
FIG. 6C illustrates this invention with a cooling sleeve and an insulator in use.
Figure 7A:
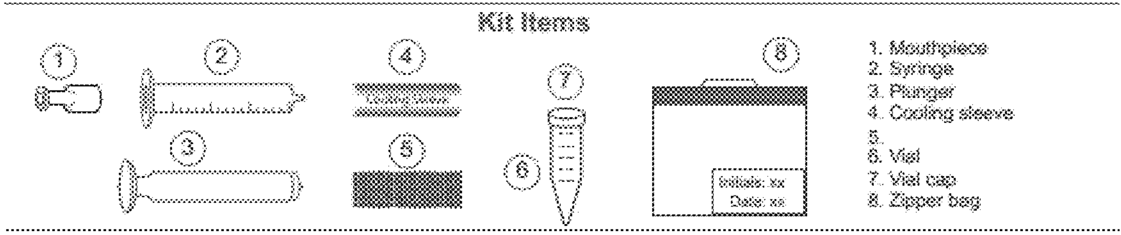
FIG. 7A-B illustrates an instruction provided with this invention.
Figure 7A:
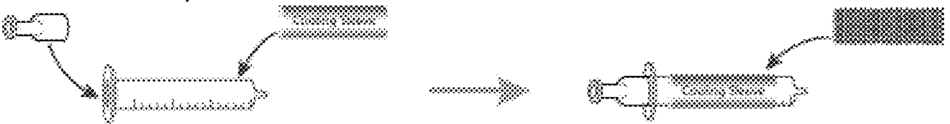
Figure 7A:
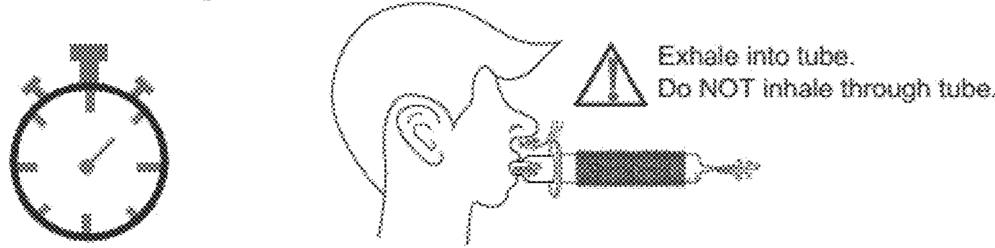
Figure 7A:
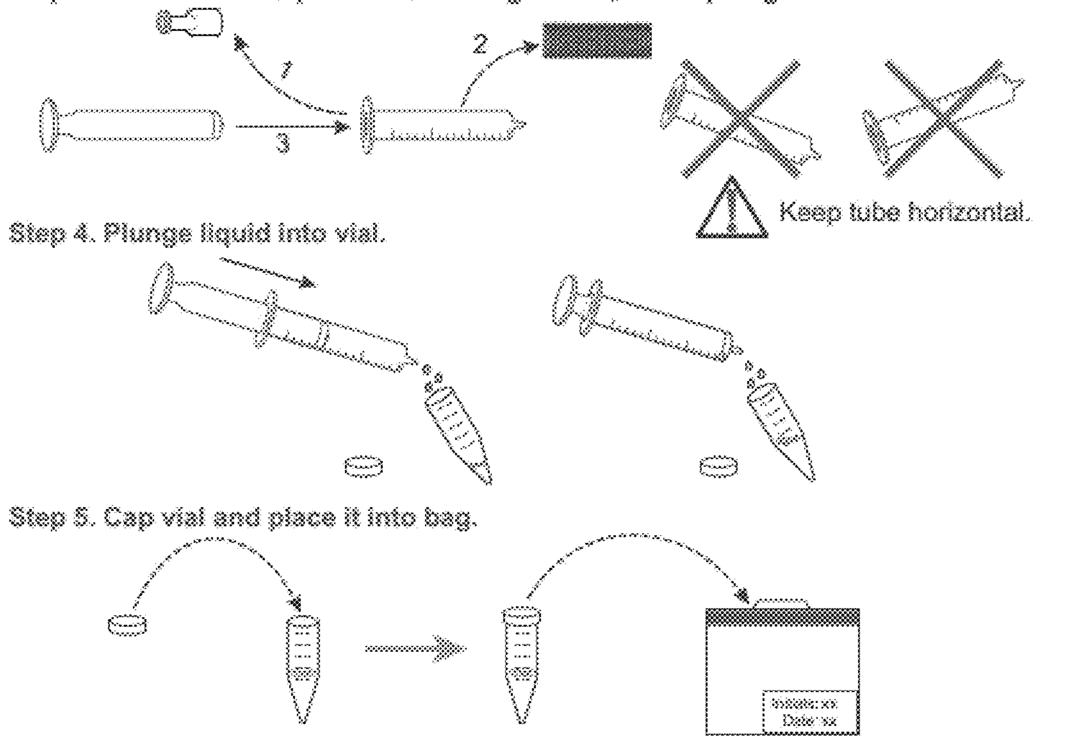
Figure 7B:
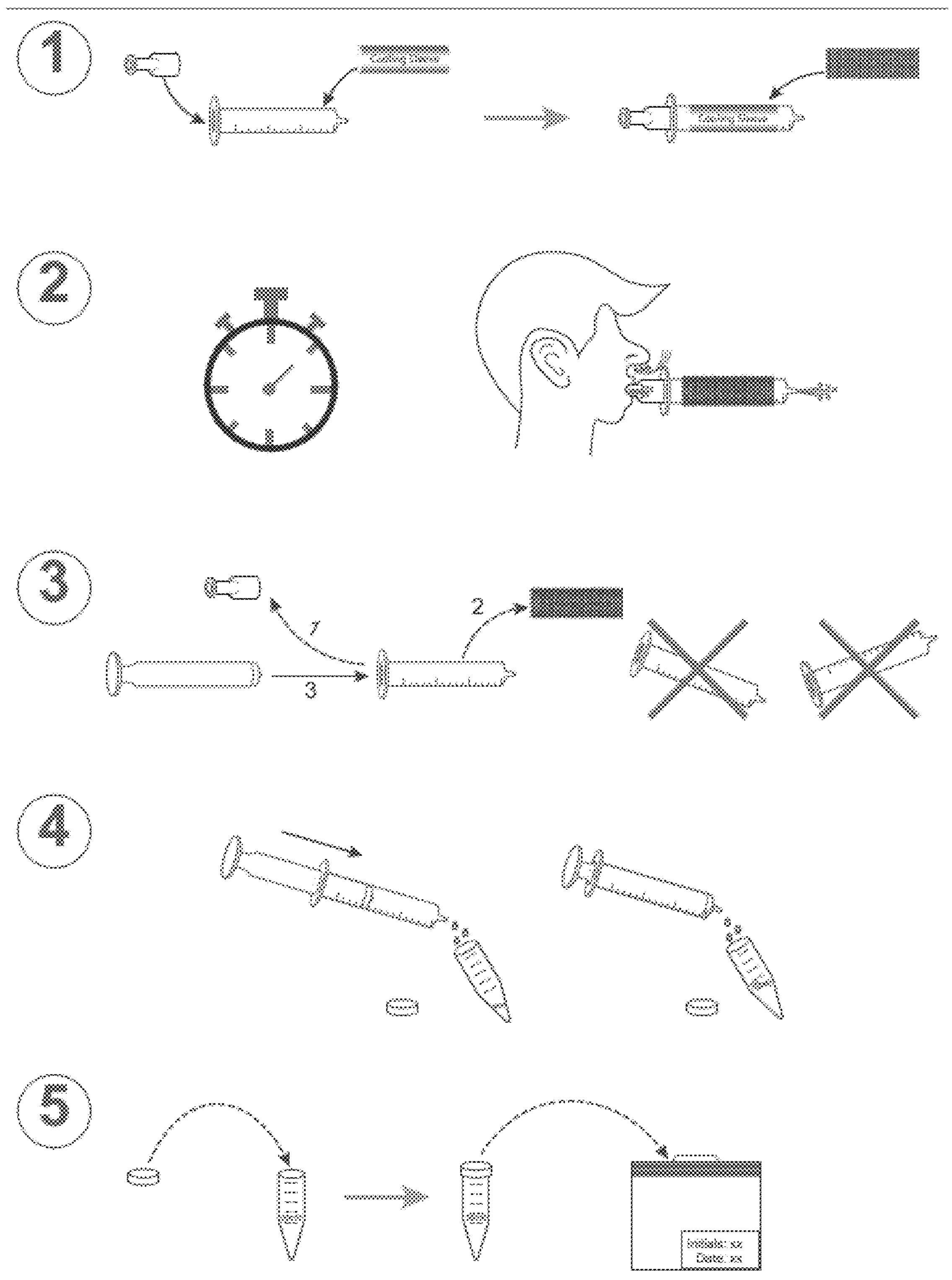

In another embodiment of the collection, the patient exhales into this invention 100 for a period of time, typically ten minutes, as shown in FIGS. 6C, 7A and 7B. The period should be timed, with the patient told to start at the beginning of the period and to stop at the end. Exhaling into this invention 100 is accomplished by: if collecting oral EBC, inhaling through the nose and exhaling through the mouth and into this invention 100 (FIG. 6C); or if collecting oral EBC without inhaling through the nose, by removing the mouthpiece 102 from the mouth to inhale, then placing the mouthpiece 102 back in the mouth to exhale into the device 100, and repeating this for each respiratory cycle; or if collecting nasal EBC, by inhaling through the mouth and exhaling through the nose and into the device 100 via a nasal mask 107; or if collecting nasal EBC without inhaling through the mouth, by removing the nasal mask 107 from the nose to inhale, then placing the nasal mask 107 back on the nose to exhale into the device, and repeating this for each respiratory cycle; or if collecting combined oral and nasal breath, by keeping the face mask fitted over the nose and mouth and inhaling either through the nose or mouth and exhaling either through the nose or mouth and into the device, as the face mask is fitted with an additional one-way valve which allows room air into the face mask during inhalation and is closed during exhalation, which forces exhalate into the device.

Breathing should be performed at a relaxed pace, with deep, full breaths: inhales should be full, filling the lungs, and exhales full, emptying the lungs; users should pause between breaths at a natural, relaxed pace in order to avoid rapid breathing which could induce discomfort and/or hyperventilation.

During the breathing session and during the condensate recovery session, this invention 100 should be held within 20° of horizontal in order to avoid sample loss through spilling out the narrow end of the tube 100. Once the breathing time period is complete, the mouthpiece/nosepiece/face mask is removed from the large end of the syringe tube 101, and the syringe plunger 104 is inserted into the same end.

The syringe tube 101 is then plunged while directing the short end of the syringe into a sample vial. As the syringe tube 101 is plunged, the exhaled breath condensate along the inner wall of the syringe tube 101 is recovered and directed out the small opening end of the syringe tube 101 and into the sample vial tube. The sample vial tube will preferably contain 1 mL of viral transport medium in the case of live virus collection, and 1 ml of denaturing molecular transport medium (such as Primestore MTM), which will lyse all cells in the sample making the sample non-infectious. The sample vial lid should then be closed, and the sample vial transported by appropriate method to a lab for analysis. The device and mouthpiece/nosepiece/face mask can then be thoroughly rinsed in cold water, air-dried, and reused by the same user.

Figure 2:
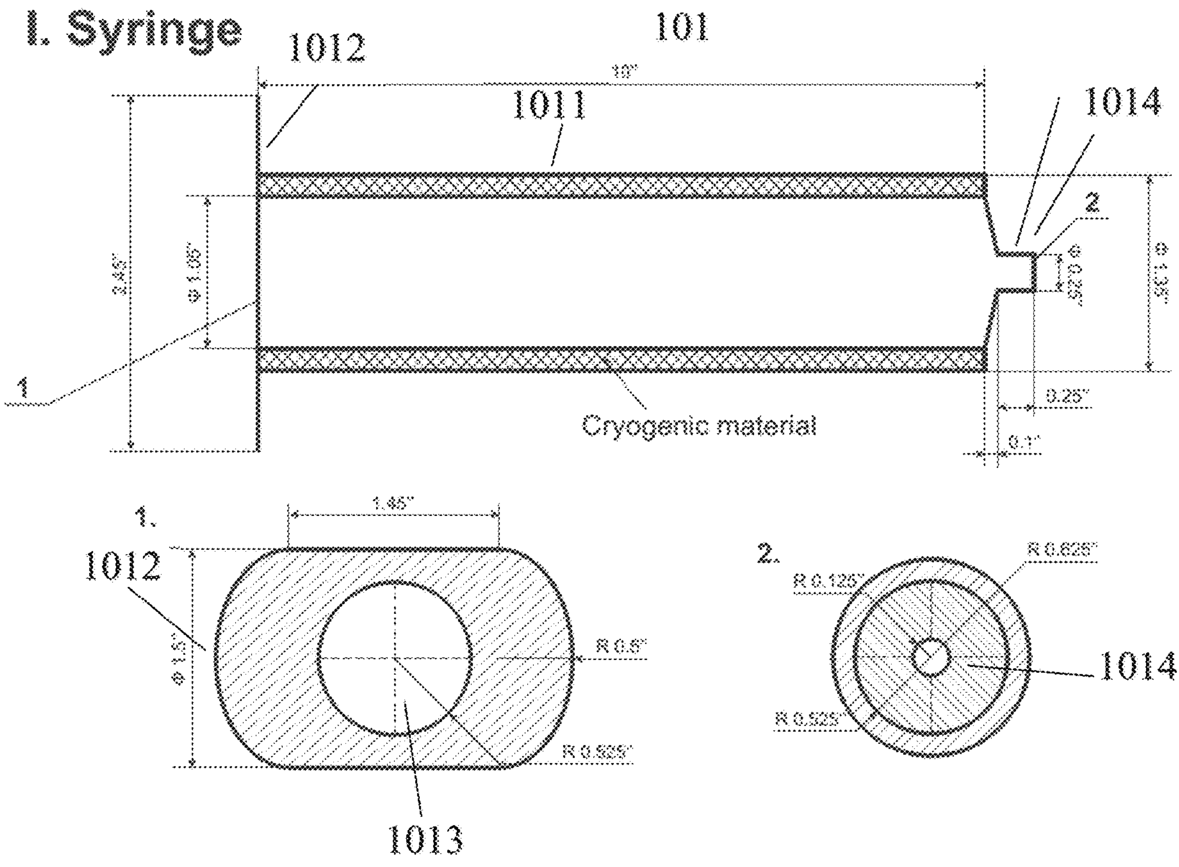
FIG. 2 illustrates a syringe of this invention.

FIG. 2 illustrates one embodiment of the syringe tube 101. The syringe tube 101 may comprise a tube body 1011, a flange 1012 surrounding a large opening 1013 at one end of the tube body 1011, and a small opening 1014 at the other end opposite to the large opening end. The large opening 1013 may be fluidly connected to the mouth piece 1012, or receives the plunger 104 so as to form an airtight connection therebetween. The small opening 1014 has a diameter that is significantly smaller than the diameter of the tube body 1011. In one embodiment, the diameter of the small opening is about 0.25 inch. In one embodiment, the diameter of the large opening 1013 is the same to the diameter of an interior space defined by the wall of the tube body 1011, which is about 1.05 inch.

Figure 3:
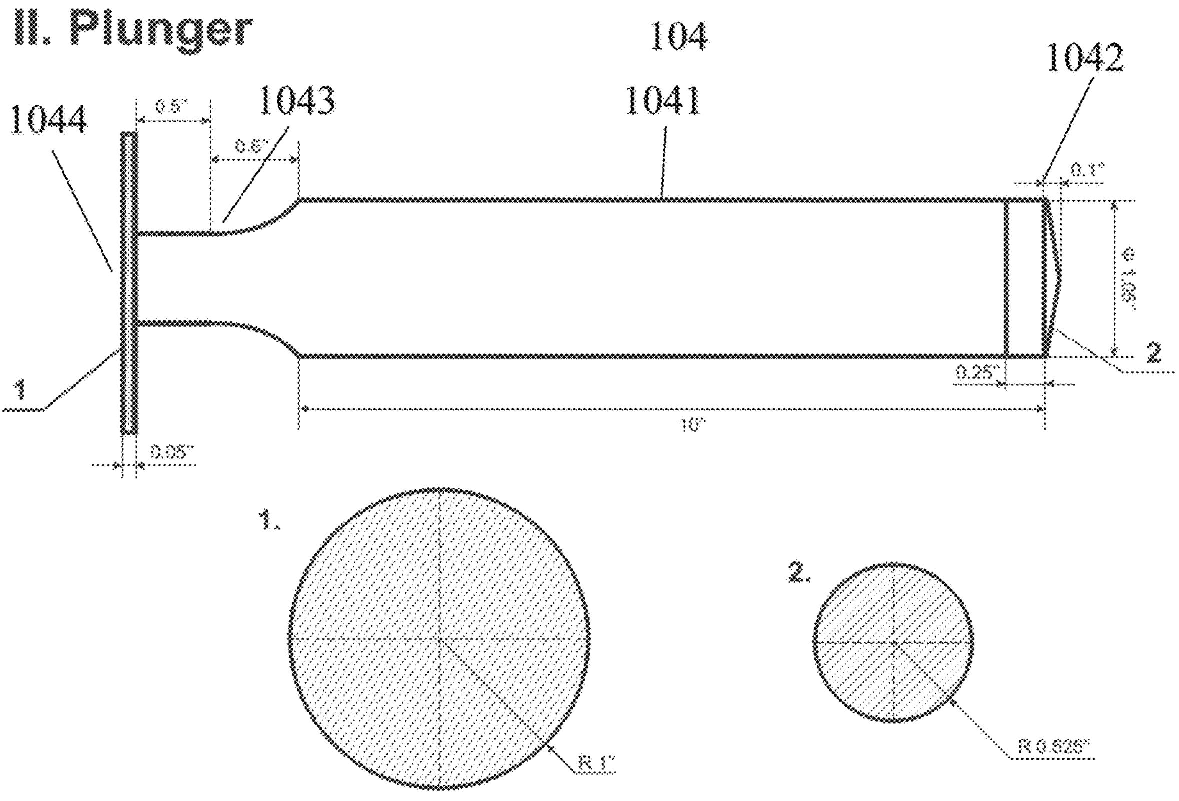
FIG. 3 illustrates a plunger of this invention.

FIG. 3 illustrates one embodiment of the plunger 104. The plunger 104 may comprise a plunger body 1041, a seal end 1042, and tapered neck 1043, and a thumb rest 1044. In one embodiment, the diameter of the plunger body and the seal end 1042 is about 1.05, such that it can be received into the interior space of the syringe tube 101. The material of the seal end 1042 is resilient such that an air-tight connection can be formed between the syringe tube 101 and the plunger 104 once the plunger is received via the large opening 1013 of the syringe 101. In one embodiment, the thumb rest 1044 may have a diameter equals to or large than that of the plunger body 1041, so as to facilitate the pushing of the plunger 104 by the patient.

Figure 4:
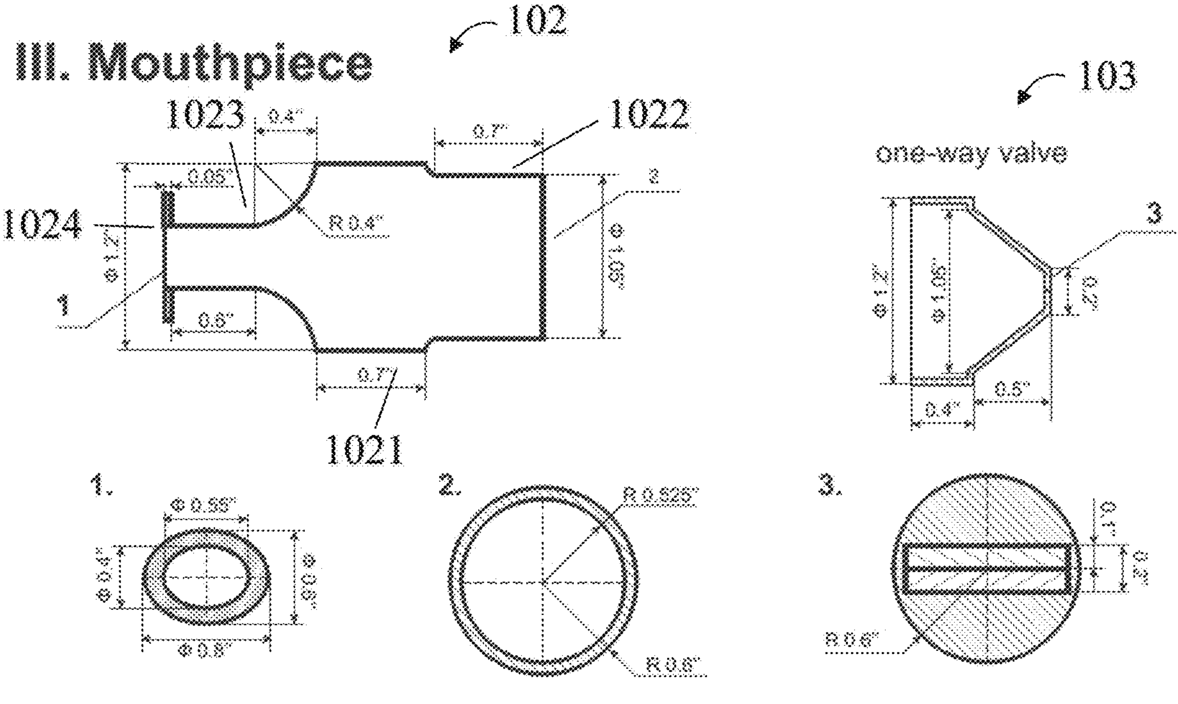
FIG. 4 illustrates a mouth piece with one-way valve, e.g. a duckbill valve, of this invention.

FIG. 4 illustrates the mouthpiece 102 and a duckbill type one-way valve 103. The mouthpiece 102 has a mouthpiece body 1021, a mouthpiece rim 1022 to be received by either the large opening 1013 of the syringe tube 101 or duckbill type one-way valve 103, a tapered mouthpiece neck 1023, and a mouth flange 1024. In one embodiment, the mouthpiece rim 1022 has a diameter about 1.05 inch, which is equal to the diameter of the interior space of the syringe tube 101 such that it can be received by the syringe 101 via the large opening 1013. In one embodiment, the mouthpiece body 1021 may have a diameter same or large than that of the mouthpiece rim. It should be noted that, in one embodiment, the diameter of the inner space of the syringe body 101, the large opening 1013, the plunger body 1041, and the mouthpiece rim 1022 should be same.

In one embodiment, the duckbill type one-way valve 103 may comprise a large valve end for receiving the mouthpiece rim 1022, and a tapered small valve end to be received by the large opening 1013 of the syringe tube 101. In one embodiment, the duckbill type one-way valve 103 is placed between the mouthpiece 102 and the syringe tube 101, forming an airtight pathway, allowing the exhaled breath to enter from the mouth flange 1024, passing through the mouthpiece 102, and enters into the syringe tube 101 for condensation through the one-way valve 103. The one-way valve 103 may prevent the backflow of the exhaled breath entered into the syringe tube 101.

Figure 5:
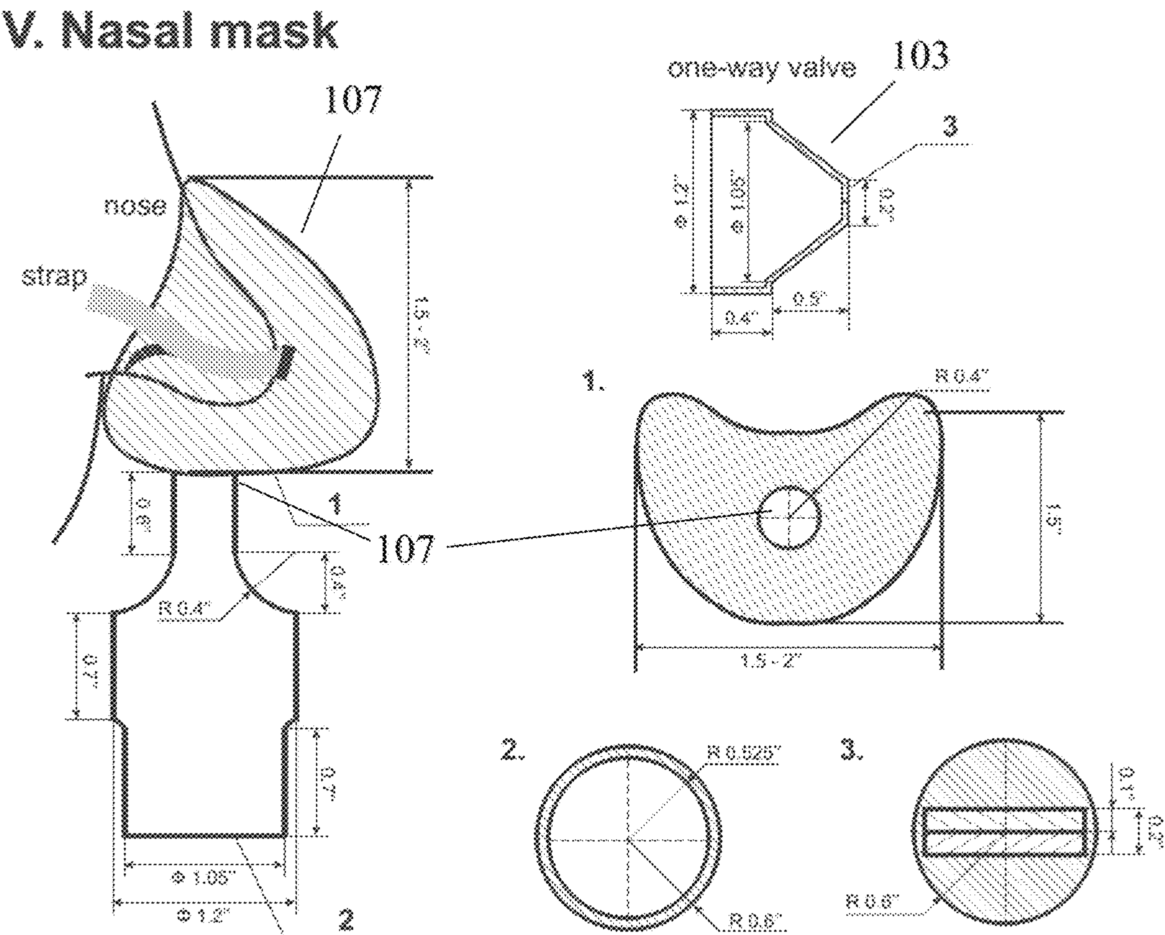
FIG. 5 illustrates a nasal piece with one-way valve, e.g. a duckbill valve, of this invention.

FIG. 5 illustrates the nasal mask 107. In one embodiment, the nasal mask 107 may comprise a nose mask covering the nose area while having a hole 1071. In one embodiment, the hole 1071 may be connected to the mouthpiece 102 by receiving the mouth flange 1024.

FIG. 14A-B illustrate one embodiment of the mouthpiece and one-way valve and the nosepiece and one-way valve, in which the one-way valve 109 is a flutter-type valve. It should be noted that the flutter-type one-way valve 109 can be used as a replacement for the duckbill type one-way valve 103 in the embodiments described for the EBC device.

In various embodiments, there are variations to the breathing tube 101, including:

A. Longer breathing tube: a tube of length of 8" to 10" may yield a larger sample in less time. In one embodiment, tube length may be varied in order to optimize volume of EBC over time.

B. Larger small opening 1014 size: a larger small opening 1014 size (at the non-mouthpiece end of the breathing tube) would vary the resistance of breathing into the device. In one embodiment, larger small openings 1014 are used, so as to maximize volume of sample over time, while maintaining ease of use.

C. Small opening 1014 placement: a small opening 1014 placed off-center, to the top of the tube, would minimize chances of accidental spilling of sample upon completion of a breath-collection session. In one embodiment, a device may include an off-center small opening 1014 for ease of use and sample collection.

D. Curved or angled exit hole (small opening 1014) tube: an exit hole tube curved or angled upward (while maintaining a consistent diameter) would minimize chances of accidental spilling of sample upon completion of a breath-collection session. In one embodiment, a device may include a curved or angled exit hole tube for ease of use and sample collection.

E. Larger diameter breathing tube: A larger diameter breathing tube offers larger surface area on which condensation can form. In one embodiment, the device may include a larger diameter tubes in order to maximize volume of sample over time.

F. Length of exit hole (small opening 1014) tube: a longer exit hole tube may offer some variations in resistance to breathing and may offer some protection against accidental spills of the sample. In one embodiment, the length of an exit hole tube may be varied in order to maximize ease of use and volume of sample over time.

G. Built-in mouthpiece: a built-in mouthpiece would increase ease of use. In one embodiment, the built-in mouthpiece still allows the plunger to enter the tube when sample collection is performed.

H. Screw-on mouthpiece: A screw-on mouthpiece would be easy to use, offering users the assurance that the mouthpiece is correctly seated.

I. One-way valve used as plunger: in one embodiment, the plunger 104 is a one-way valve 103 that could remain in the breathing tube and be pushed through the tube to perform the plunger ruction in order to collect the sample. This would increase ease of use.

J. Filter tip: A filter fitted on the small end of this invention, such that the filter does not prohibit exhalation through the device but does cause all substances or particles smaller than the filter size—such as small aerosols or droplets, or virions or other pathogens—to be retained within the device or trapped by the filter material. The filter material is added to the sample at the end of the sample collection time by removing the filter prior to plunging the EBC sample, and submerging the filter in viral transport medium or molecular transport medium; or scraping the filter with a flocked swab or other instrument in order to recover all sample from the filter and placing the swab or other instrument in viral transport medium or molecular transport medium. This use of this invention would ensure that no substances or particles smaller than the filter size exit the invention during a breathing session.

In one embodiment, the cooling sleeve 105 contains various configurations so as to maximize ease of use. The variation on the configurations may include the following.

A. Integrated (built-in) cooling material, in a cavity between the inner wall of the syringe tube 101 and an outer wall. Such a design would allow the user to place the entire device in the freezer, would avoid the step of placing the cooling sleeve 105 on the tube 101, and would increase intuitiveness and ease of use.

B. Cooling cylinder with chemically induced cooling: the cooling sleeve 105 would contain two chemicals in separate packets, design to be broken and mixed, that react to mixing by producing a cooling reaction. Such a design would allow users who don't have ready access to freezing to use the device, increasing the portability and reach of use of the device.

C. Various methods of attaching the cooling sleeve 105: the current method uses a cooling sleeve, which rolls onto the tube. Other designs may include a wrap-around sleeve, or a series of smaller "donuts", which would allow variable lengths of cooling.

In one embodiment, the caps for the ends of the syringe tube 101 may include caps for the two ends of the syringe tube 101, so as to maintain a sterile interior of the tube until use.

In one embodiment, a collection vial may be attached to the end of the syringe tube 101. The vial would be attached in such a manner that it swings out of the way during use of the tube (when the user is breathing into the tube), and can be swung into place for sample collection once the breathing session is complete. After the user plunges the liquid sample into the vial, the vial would be easily snapped off of the tube 101, capped with an attached cap, and mailed in for analysis.

In one embodiment, a mass flow meter may be built in the collection devices. A version of the device designed for research or clinical use would have a mass flow meter slot in between the mouthpiece and the breathing tube. The meter would measure the flow of exhaled breath, in order to produce an accurate measure of the amount of air exhaled into the device. Because of cost, such a device would be intended for research or special clinical use.

After the vial containing the collected EBC is received by a laboratory, the sample can then be analyzed for the presence of SARS-CoV-2 or other respiratory pathogen using any available method for detecting the pathogen, e.g., targeting its DNA, RNA, proteins or any other suitable feature. In one embodiment, first the sample is pipetted out of the sample vial and into e.g. an Amicon Ultra-4 3 kDa, or other size, filter and centrifuged according to the manufacturer's instructions until the sample is filtered to a volume of 100-200 microliters. The filtered sample is pipetted from the filter into a 1.5 mL vial, and then the RNA is extracted. In one embodiment, the RNA is extracted conventionally from the sample using the Qiagen QIAamp MinElute Virus Spin Kit, according to the manufacturer's instructions. Preferably, in the final step the sample is eluted in 40 microliters of elution buffer.

The amount of RNA in the sample is then conventionally determined with either real-time reverse-transcriptase quantitative polymerase chain reaction (rRT-qPCR) or reverse-transcriptase droplet digital polymerase chain reaction (RT-ddPCR) using Taqpath 1-Step RT-qPCR Master Mix CG (Thermofisher), according to the manufacturer's instructions in each case. In the first case of RT-qPCR, for each sample, cycle threshold (CT) values are obtained and compared to a standard curve in order to calculate absolute quantification of viral RNA in the sample. In the second case of RT-ddPCR, absolute quantification of viral RNA in the sample is directly determined.

Whereas this invention has been described herein with particular reference to SARS-CoV-2, it is fully applicable to other respiratory pathogens (viruses and microorganisms) as well. These include both upper and lower respiratory tract pathogens, other viruses, bacteria, fungi, etc.

Viral pathogens, include rhinoviruses, respiratory syncytial virus, influenza virus e.g., avian influenza viruses (such as H5N1 and H7N9), parainfluenza virus, human metapneumovirus, measles, mumps, adenovirus, and coronaviruses (e.g., MERS-CoV, SARS-CoV-1, etc), etc.

Bacterial pathogens may be less common than viral but include *Streptococcus pneumoniae, Mycoplasma pneumoniae, Haemophilus influenzae*, and *Chlamydophila pneumoniae. Coxiella burnetii, Mycobacterium tuberculosis* and *Legionella pneumophila*, etc. Respiratory fungal pathogens include Aspergillus, Cryptococcus, Pneumocystis, etc.

Bacterial sinusitis, bronchitis, or pneumonia and the like may also occur secondarily after a viral respiratory infection. Any one or more suspected pathogens can be tested for in a given sample.

Relevant respiratory diseases are all those corresponding to the respiratory pathogens mentioned and to any other, such as chickenpox (varicella), coronavirus infections (e.g., COVID 19), diphtheria, Group A *Streptococcus, Haemophilus* influenza type b, influenza (flu), Legionnaire's disease, measles (rubeola), Middle East Respiratory Syndrome (MERS), mumps, pneumonia, pneumococcal meningitis, German measles (rubella), Severe Acute Respiratory Syndrome (SARS), tuberculosis, whooping cough (pertussis), aspergillosis, cryptococcal meningitis, Pneumocystis pneumonia, etc.

Animal-borne infectious disease pathogens are also included within the scope of this invention. Examples include anthrax, brucellosis, hantavirus, psittacosis, plague, Q-fever, tularemia, etc.

These and other aspects of the present invention are further described below. Without intent to limit the scope of the invention, exemplary instruments, apparatus, methods and their related results according to the embodiments of the present invention are given below. Note that titles or subtitles may be used in the examples for convenience of a reader, which in no way should limit the scope of the invention. Moreover, certain theories are proposed and disclosed herein; however, in no way they, whether they are right or wrong, should limit the scope of the invention so long as the invention is practiced according to the invention without regard for any particular theory or scheme of action.

Example 1

In one embodiment of the invention the method may include the following procedures.

This invention in a kit such as that of FIG. 1A, may be delivered to a Covid-19-positive patient's residence, who may be in-home quarantine/isolation. In order to minimize risk of exposure to infection during delivery of the kit, delivery will preferably involve no contact with the patient. In order to achieve this, the package should be delivered by private courier or in a similar manner to the patient's door: e.g., place the package outside the front door of the patient's residence, leave the site, then alert the patient by phone to retrieve the package.

Once the patient receives the kit, the patient will be scheduled to perform the EBC collection procedure under the guidance of a remote online videoconferencing with an instruction team which may comprise one or more health care providers, a medical professional, research staff, etc. Through the videoconference, the patient will be informed of the steps of collecting the sample, e.g. nasal or oral breath condensate. In one aspect of the invention, at least one member of the instruction team will be trained concerning infectious agent packaging and shipping. The patient will then be instructed over the videoconferencing on proper packaging of the sample for transport, including full compliance with the Category B, or any applicable, guidelines.

In one embodiment of the invention, the sample packages can then be placed outside the patient's residence for pickup by a courier. In one aspect of the invention, the courier is trained in Category B packaging. In one embodiment, the courier will disinfect the package with disinfectant such as alcohol spray prior to touching it, and will then transport the completed samples directly to a lab. In one embodiment, the lab is authorized to handle samples from potential Covid-19 patients.

In one embodiment, samples will be opened and moved through the analysis pipeline exclusively by trained and certified staff for working with human viral infectious agents. In one embodiment, the results will be analyzed in the lab receiving the package. In another embodiment, the result will be electronically transmitted to another lab for data analysis.

In one embodiment, the EBC collection kit may include one or more items of the following: a consent form, written instructions, components of a smell test, a sample collection kit, a sample packaging kit, etc.

In one embodiment, the sample collection kit may include one or more items of the following: one or two of this invention's EBC collection tubes 100, for oral or nasal EBC if one tube is included, or both if two tubes are included; one nasal mask 107 for use during nasal EBC collection, disposable cooling sleeves 105, a marker pen, a BD universal viral transport collection kit (or the equivalent), and alcohol wipes.

In one embodiment, the sample packaging kit may include a shipping system, e.g., a Therapak Biological Substance Category B Ambient Shipping System package (or the equivalent), including all packaging and labeling required.

In one embodiment, the procedure for sample collection may include one or more steps as described below.

Upon receipt of the EBC collection kit, the patient can be contacted by phone, texting, messaging or other electronic communication method to begin the procedure. In one aspect, the patient will be instructed to immediately place the cooling sleeves 105 and shipping cool-packs in the freezer for later use.

In one embodiment, the first step will be consent. Consent forms will be provided in two ways: a digital PDF copy will be emailed to patients prior to delivery of the sample collection kit, and a paper copy of the consent form will be included in the EBC collection kit. Patients will be instructed by phone, text messaging, or other electronic communication to open the package and retrieve the consent form, which will be on the top of the contents of the package. A consenting study team member will go over the consent form with the patient by phone, text messaging, or other electronic communication describing the study procedure, answering any questions the patient has, and giving the patient as much time as needed to read the consent form. Signatures will be collected digitally on the emailed PDF consent form. The patient will keep the paper copy of the consent, and will be emailed a fully signed copy of the consent, and/or mailed a fully signed paper copy.

In one embodiment, the next step will be survey completion and smell testing if this option is included. The survey (and conventional smell test) will be provided over the videoconference in order to avoid researcher contact with surfaces the patient has touched.

In one embodiment, the next step will be sample collection. Once the patient consents to participation, a video conference for the sample collection will be started. In one embodiment, the video conference can be conducted using Zoom or an equivalent service. Over the video conference, the patient will be instructed by the instruction team to remove the contents of this invention in kit form, and to confirm that all items are present. The patient will be familiarized with the data collection procedure by going over each item in the kit. In one embodiment, the patient will be instructed on how to make regular, consistent inhalations and exhalations through the nose and mouth, and will have ample opportunity to practice this procedure prior to the collection step while receiving feedback from the instruction team.

In one embodiment, the patient will then perform one or more EBC collection sessions. In one embodiment, each EBC collection session will be about 10 minutes. In one embodiment, there should be two to four EBC collection sessions performed. Half of the sessions will include nasal breathing and the other half will include oral breathing. The patient will be monitored by the instruction team, who will provide feedback in order to keep the patient's breathing at a slow, comfortable, natural pace.

In one embodiment, this invention 100 is designed such that the patient can breathe naturally while using it, both in the inward and outward directions. Subjects will be seated comfortably and asked to breathe naturally for up to 10 minutes into this invention 100, through either an attached nasal mask 107 or an attached mouth piece 102. During the collection procedures, the instruction team will observe and monitor the patient to be sure this invention 100 is properly used. In one embodiment, the breath samples will be collected from a patient who seats comfortably and performs tidal breathing through the nose or mouth.

In one embodiment, the next step is sample packaging. The patient will perform packaging under the video supervision of at least one member of the instruction team who was trained in Category B packaging. For each sample collected, the patient will move the sample from the collection tube into the leak proof BD universal viral transport vial and enclose the top of the vial. In one embodiment, the patient will label the vial with a de-identification code, with the provided marker.

In one embodiment, the patient will then use the included shipping kit. In one embodiment, the patient will place the vial in a secondary leak proof container along with absorbent material, and seal the secondary container. In one embodiment, the patient will properly label the secondary container using materials provided in the kit, then will wrap the secondary container with provided cushioning material, place it in the provided shipping box, and seal the box. The shipping box will be properly labeled prior to sending the kit out In one embodiment, the instruction team will coordinate timing of pickup with the courier, and will instruct the patient to place the box outside the front door just prior to the arrival of the courier. In another embodiment, a separate agent will coordinate timing of pickup with the courier.

In one embodiment, the packaged samples will be picked up by an approved hazardous materials courier and transported directly to the lab for analysis using methods and pipelines already in place for testing of COVID-19 samples.

With respect to the present invention, in one embodiment, the experimental tasks will take place in the patient's home over videoconference. The videoconferences can be recorded (audio and video) in order to document compliant participation and to ensure patient safety. In one embodiment, recordings may be used by researchers in data analysis to investigate differences in performance of the task between patients and in published research if needed for publication purposes. In one embodiment, the recording will be stored on a secure server, with access only by research members, and will be destroyed at the end of the study.

In another embodiment, the patient will perform the aforementioned sample collection process using the guidance provided on an instruction manual rather than a video conference.

In another embodiment, the patient will perform the aforementioned sample collection process using the guidance provided in an online video instruction rather than a video conference.

In another embodiment, the patient will perform the aforementioned sample collection process using the guidance provided in an online audio instruction rather than a video conference.

In one embodiment, the patient samples will be analyzed using rRT-qPCR. The samples will be analyzed within 72 hours of the completion of collection by a lab. In one embodiment, the lab is a lab certified to handle biological specimens from potential Covid-19 patients.

Compared to other currently home administered Covid-19 sample collection methods, such as a nasal swab performed by the patient at home, which are technically difficult to perform and could be dangerous to be self-administered, the method of the present invention overcomes these challenges and limitations by offering a simple and noninvasive technique that can easily be collected at home.

In one embodiment, this invention in a kit will also be mailed to a number of healthy volunteers. The healthy volunteers will perform the same sample collection steps, either supervised or not supervised by the videoconference. The healthy volunteers will then mail the samples back to a lab. These testing sessions will be videotaped, and the success of the sample collection will be assessed to identifying common errors made during the sample collection procedure. The kits and the instructions provided in the kits will be optimized based on the common errors identified therein.

Example 2

The EBC collection of this invention has been performed by 3 patients who tested positive for COVID-19, and 12 EBC samples have been collected from the 3 patients. A video conference was held and the patients were guided through the process samples from their own homes during self-quarantine. Each patient provided 4 samples, including 2 nasal breath samples and 2 oral breath samples. Samples were processed by a certified laboratory, including RNA extraction and PCR. The testing procedure used the same steps that have been approved for hospital patient testing. SARS-CoV-2 virus was detected in 4 out of 4 samples for subject 1, 2 out of 4 samples for subject 2, and 0 out of 4 samples for subject 3. See Table 1 which reflects CT values for each sample. In subjects whose viral load was still high enough for detection, CT values were generally below 30, suggesting robust viral levels in the samples.

TABLE 1

| | | | | | Results N1 | | Results RP | |
|---|---|---|---|---|---|---|---|---|
| Subject | Type | Label | Source | Time | Mean | SD | Mean | SD |
| 1 | MTM | E | Nasal | PM | 29.580 | 0.003 | 35.678 | 0.963 |
| | | F | Oral | PM | 28.758 | 0.053 | 33.658 | 0.429 |
| | | G | Oral | AM | 30.935 | 0.085 | 32.458 | 0.287 |
| | | H | Nasal | AM | 29.490 | 0.097 | 31.578 | 0.064 |
| 2 | MTM | I | Nasal | PM | 37.360 | N.A. | 34.927 | 0.134 |
| | | J | Oral | PM | 37.326 | N.A. | 36.840 | 0.414 |
| | | K | Oral | AM | N.A. | N.A. | 34.976 | 0.150 |

TABLE 1-continued

| | | | | | Results N1 | | Results RP | |
|---|---|---|---|---|---|---|---|---|
| Subject | Type | Label | Source | Time | Mean | SD | Mean | SD |
| | | L | Nasal | AM | 37.544 | N.A. | 36.145 | 0.704 |
| 3 | MTM | M | Oral | PM | 27.469 | 0.002 | 31.503 | 0.353 |
| | | N | Nasal | PM | 27.820 | 0.046 | 32.960 | 0.351 |
| | | O | Nasal | AM | N.A. | N.A. | 29.256 | 0.077 |
| | | P | Oral | AM | 38.320 | N.A. | 31.162 | 0.003 |
| Positive control for all above | | | | | 34.305 | N.A. | 30.027 | N.A. |

In an optional version, the foregoing example is conducted by patients themselves using the provided instructions without supervision.

Example 3

Figure 8:
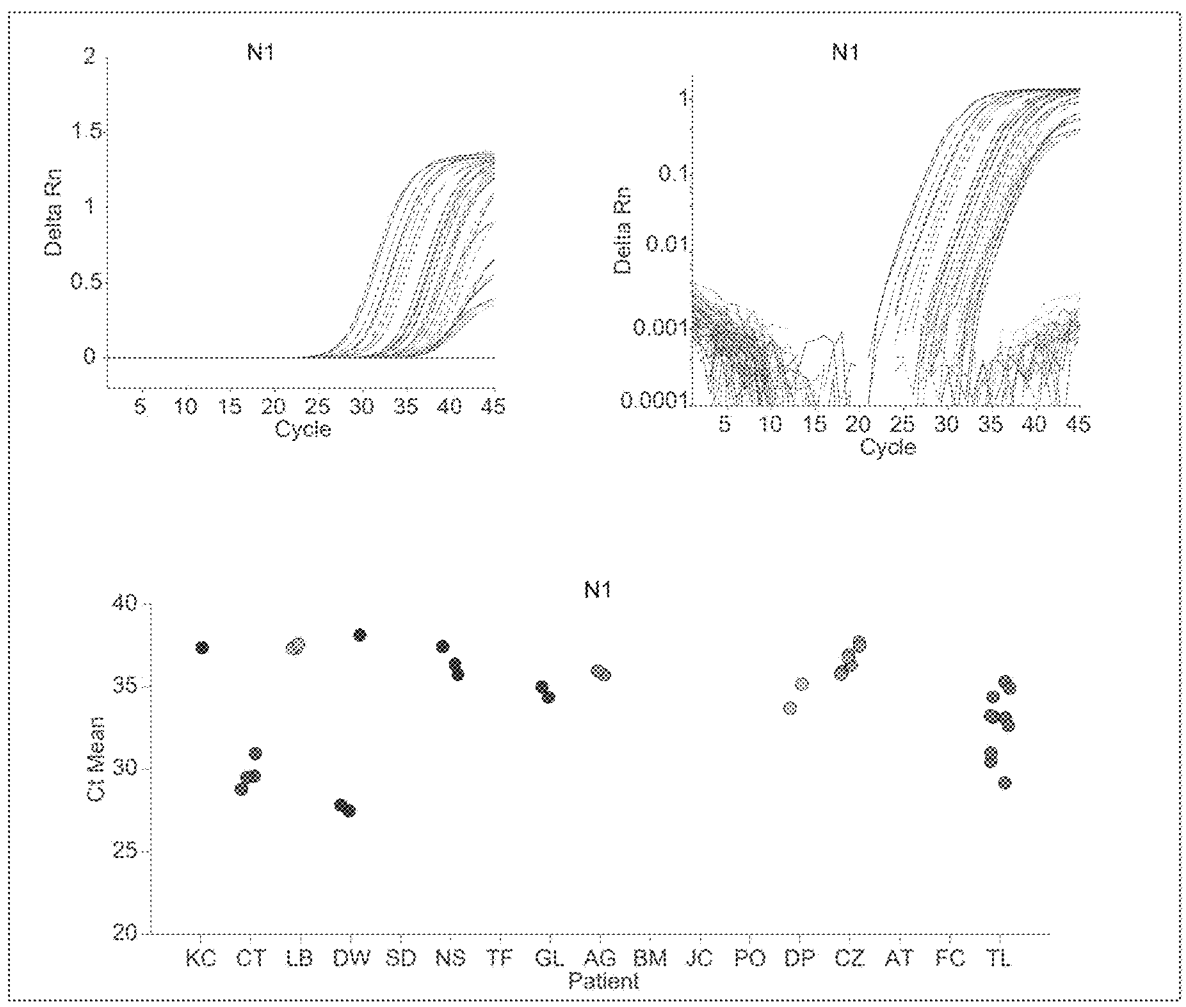
FIG. 8 illustrates linear curves and log curves of a viral RNA target (N1) from samples collected with this invention from 17 Covid-19 positive individuals, as well as the mean cycle threshold values for each sample for each patient.

Samples of 17 COVID-19 positive patients were collected using the apparatus and method described above, and the samples collected were analyzed using real time quantitative PCR (RT-qPCR), in triplicate. Highly specific Taqpath assay was used, which is the same assay used for clinical samples. As can be seen in the FIG. 8, SARS-CoV-2 is detected in most samples analyzed. The upper panels show amplification curves for viral RNA target (N1) from all samples analyzed. On the upper left are the linear curves and on the upper right are the log curves. As can be seen in FIG. 8, good amplification is evident with parallel curves, suggesting robust results.

The lower panel shows the mean cycle threshold values for each sample for each patient. Each column is one patient, and each dot is the mean CT value for each of their samples. As can be seen in the figure, patients performed different numbers of sample collection sessions. Some patients performed multiple collections, and there are different numbers of samples across patients. Overall, consistent results are found within patients for multiple runs collected on the same day. It is also apparent in the FIG. 10A that the SARS-CoV-2 virus is not detected in a patient who tested positive via nasopharyngeal swab. However, this patients was on Day 11 since symptom onset, and was thus likely not shedding virus on breath during the breath sample collection. It would also be expected that asymptomatic and long-term positives (meaning they had tested positive for COVID-19 for weeks, sometimes months) would have measurable virus on internal swab tests for days, weeks or months after they had stopped shedding virus on breath. The method and the apparatus of the present invention can thus detect the virus in exhaled breath condensate in most patients and the levels detected vary across individuals. While some individuals have very high levels of virus in their breath, others have very low levels, and some, none at all. In one embodiment, this levels of virus detected indicates how contagious an individual patient is as described herein.

Figure 9:
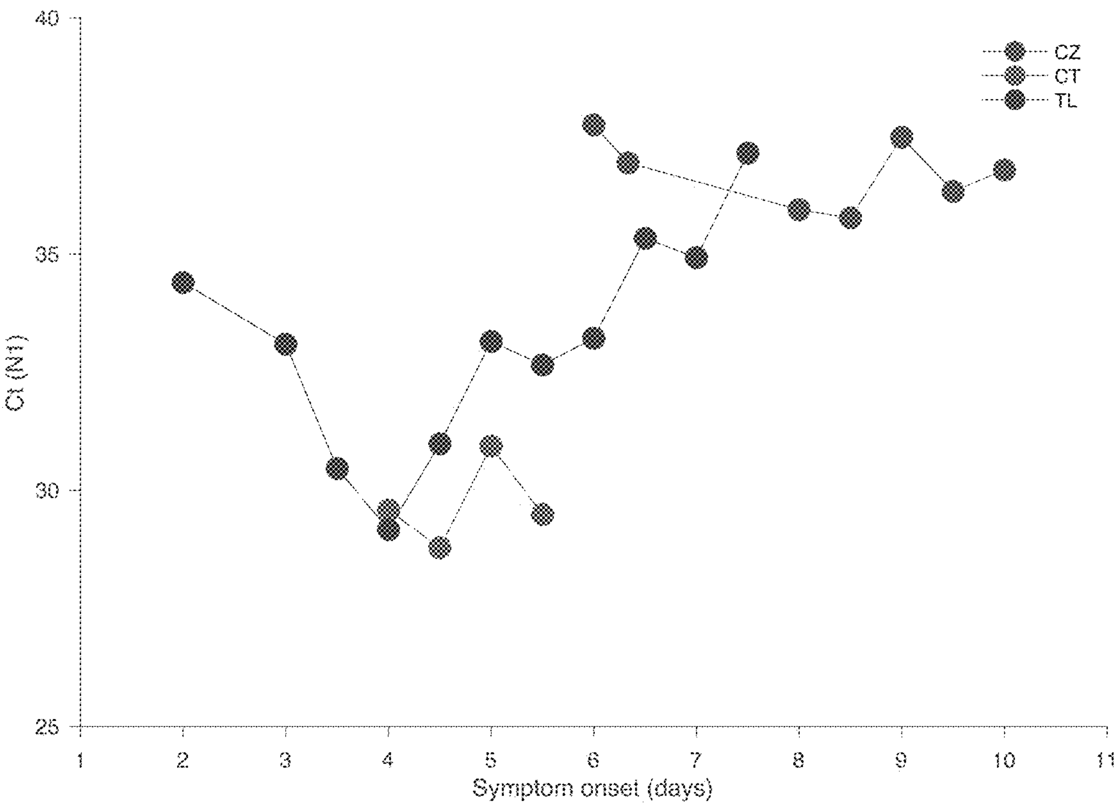
FIG. 9 illustrates how levels of viral shedding on breath change over the course of the disease using data from samples collected with this invention.

FIG. 9 shows how levels of viral shedding on breath change over the course of the disease. Several COVID-19-positive participants produce 2 samples per day over several days during self-isolation at home. Results from this longitudinal study are shown in FIG. 9 which shows CT values plotted against days since symptom onset. As can be seen in the figure, patient TL began collecting samples at day 2 post-symptom onset. It is found that viral levels on exhaled breath increased up to day 4, when the virus peaked, and then began to decrease up to day 7, when the patient stopped producing samples. SARS-CoV-2 virus is detected in all of her samples, and therefore did not reach a point where virus was no longer detected in the exhaled breath.

Patient TL was asymptomatic in last day of collection, but the patient was still shedding virus in the exhaled breath. Notably, after the patient's final set of samples (in full PPE) was picked up, it is observed the patient stopped the self-quarantine and joined social activity without social distancing. This demonstrates and emphasizes the public health risk of symptom-free patients assuming they are no longer contagious. Similarly, the virus is detected in all samples from patient CZ, who produced samples up to day 10 post-symptom onset.

It can be seen likely that exhaled breath is a very significant, if not the most significant, transmitting mechanism of this disease. Therefore, longitudinal data such as this are extremely valuable for understanding how this disease spreads.

Notably, variability across patients in levels of SARS-CoV-2 in exhaled breath condensate are found. CT values ranged from 28.8 all the way to non-detectable (above 40). This indicates that COVID-19 patients shed variable levels of virus on their exhaled breath, suggesting variable levels of contagiousness across patients.

As such, it is concluded that using the method and apparatus described in the present invention, the SARS-CoV-2 virus is detected in the exhaled breath of COVID-19-positive patients. In addition, viral shedding into exhaled breath condensate is variable across patients, suggesting differential disease stages, and, it is expected, differential contagiousness.

Example 4

In one embodiment, a direct comparison of exhaled breath sample type to the nasopharyngeal sample type is established in a baseline validation study.

EBCs samples are collected from patients who have been swabbed for COVID-19 in a conventional setting, immediately following their nasopharyngeal swab test result. By collecting samples within a very short time window, comparing test results directly between the two sample types can be accomplished, because patients are shedding roughly the same viral load within this time window. This provides a method to provide a baseline validation of the sample type (EBC) relative to the standard type (nasopharyngeal swab), and provides a method to determine the relative sensitivity and accuracy of the exhaled breath sample in detecting SARS-CoV-2.

Experiment 1 design: The sample collection device consists of a 60 mL tube, a plunger 104 with outer diameter equal to the inner diameter of the syringe tube 101, and a tubular gel-style cooling sleeve 105 that fits over the tube 101. Patients will breathe into the tube 101 for 5 minutes during downtime in the location where the conventional testing occurs, such as an ER or a clinic. Liquid will then be plunged out of the tube 101 into a sample vial containing molecular transport medium designed to inactivate the virus and preserve nucleic acid integrity (e.g., Primestore). Aside from delivering this invention in a kit 101 contents and retrieving completed sample vials, experimenters conduct the collection from outside the patient's room over the phone.

EBC samples are collected in two sets of patients. Each set includes 24 COVID-19-positive patients, and 24 COVID-19-negative patients, consistent with or exceeding the sample size for published early COVID-19 research studies. Samples will be analyzed using the Taqpath assay in a conventional manner, e.g., on the QuantStudio 7 Flex system (ThermoFisher). Steps include microcentrifuge filtration (3 Kda filter size), followed by RNA extraction, followed by RT-qPCR. Samples are analyzed using one of three different nucleic acid-based platforms (Cepheid GeneXpert SARS-CoV-2, BioRad CFX Seegene Allplex 2019-nCoV5 and Roche Cobas 6800 SARS-COV-2). Typical EBC samples are between 1 and 2 mL in volume. The GeneXpert SARS-CoV-2 assay requires 300 μl of specimen, the Seegene Allplex 2019-nCoV assay uses 50-100 μl, and the Cobas 6800 SARS-CoV-2 assay requires 400 μl. This relatively large sample size allows the samples to be run on all three platforms.

Results of the tests are used to compare with clinical nasopharyngeal swab results to EBC sample results using the same analysis method. Positive results should be found from all EBC samples from patients with positive nasopharyngeal swab results. This validates the method of this invention as a new clinical diagnostic tool. The test could also be used to estimate transmissibility of SARS-CoV-2 through exhaled breath.

Experiment 2: Comparison of false negative rates between EBC samples and nasopharyngeal swab samples.

NPSs obtain samples from a small portion of the nasal cavity, specifically only the tissue that makes contact with the swab. By contrast, EBC samples pull from the entire respiratory airway, including deep and superficial lung tissue, nasal cavities and oral cavities. This is an important distinction between the sample type of the present invention and the standard clinical sample type, because individual patients may have different anatomical distributions of viral load along the respiratory airway. This means that a nasopharyngeal swab sample might only make contact with a part of the airway that happens to contain no virus, even if virus is present in other areas (for example deep inside the lung), leading to a false negative result. It is predicted that the EBC samples will ameliorate this issue by containing virus stemming from the entire respiratory airway. Therefore, individual variation in anatomical location of virus along the airways will have far less of an impact on the EBC than NPS approach.

The patients are recruited among those tested NPS-negative for the virus to preferentially include those who are suspected to be positive by their physician. This identifies cases where the nasopharyngeal swab yielded a negative test result, but the EBC sample yielded a positive result. EBC samples can yield a smaller number of negative results than the nasopharyngeal swab, based on the fact that it pulls from the entire respiratory airway. This would suggest that the EBC sample provides a more sensitive measure of viral load in COVID-19 patients.

Figure 10A:
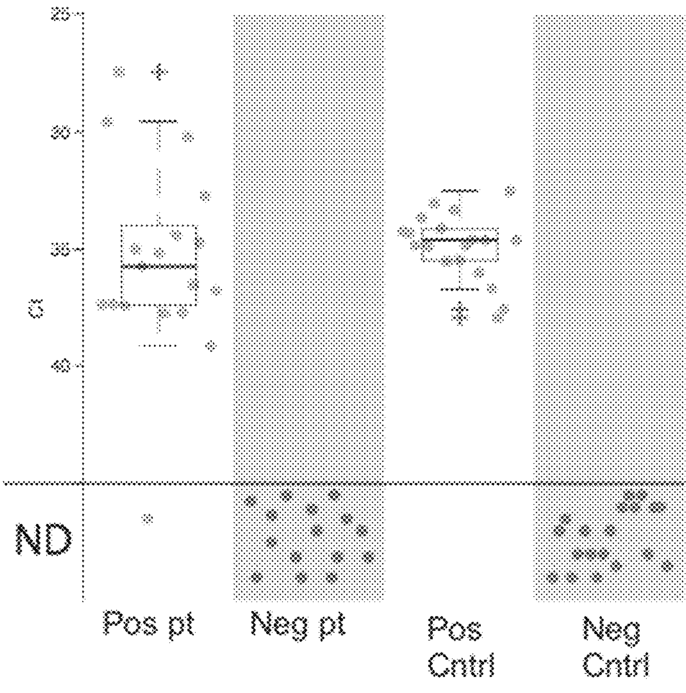
FIG. 10A-B illustrates the accuracy and sensitivity of this invention in detecting SARS-CoV-2 RNA in exhaled breath samples.

The COVID-19 testing protocol at Northwestern Memorial Hospital (NMH) includes collection of a nasopharyngeal swab which is then submitted for analysis by the Abbott Now Rapid Nucleic Acid based test, which provides binary results (positive or negative). As shown in FIG. 10A, in same day testing, using this invention 100 and related collection method, SARS-CoV-2 RNA was detected in 17 out of 18 exhaled breath samples that were collected from patients who tested positive for COVID-19 (notably the one breath sample in which SARS-CoV-2 RNA was not detected was from a patient on Day 11 since symptom onset, and was likely not exhaling virions even though they were present at his swab site), and in zero out of 15 samples that were collected from patients who tested negative for COVID-19.

Figure 13:
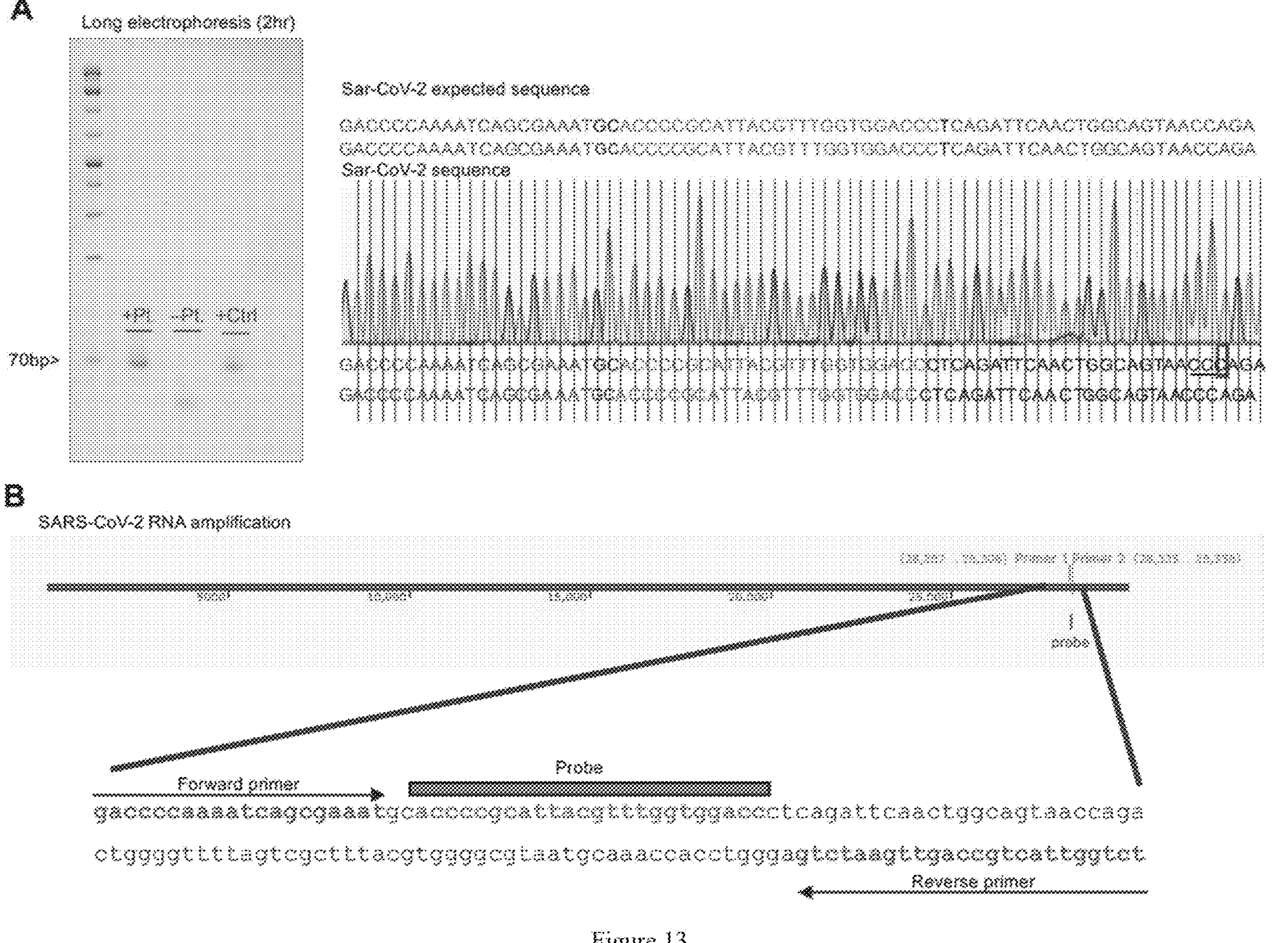
FIG. 13 illustrates electrophoresis and sequencing of PCR product were performed to confirm results from samples collected with this invention.

The RNA detection is performed to confirm the results, using electrophoresis and sequencing of PCR product, as shown in FIG. 13. The electrophoresis and RNA sequence result are reflected on the upper panel of FIG. 13, and the forward and reverse primer, as well as probe sequence, are reflected in the lower panel of FIG. 13.

Figure 10B:
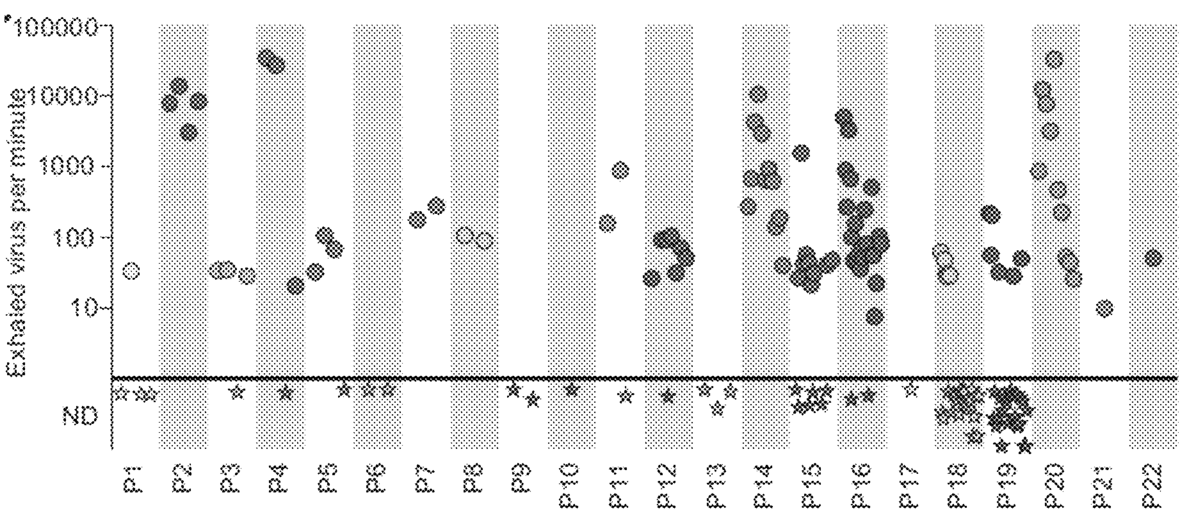

FIG. 10B illustrates the exhaled virus per minutes of each of the 22 patients among the 23 patients who tested positive for COVID-19.

Figure 11A:
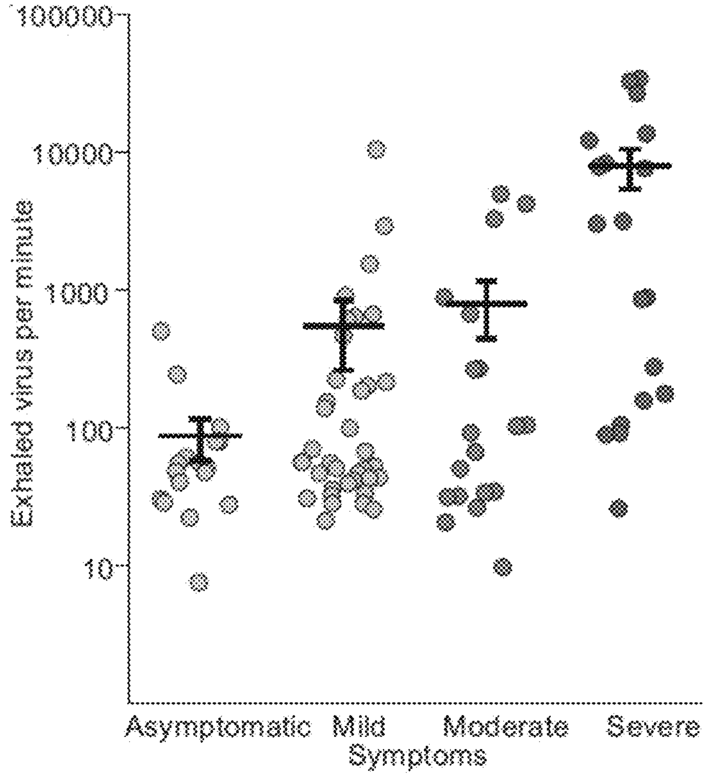
FIG. 11A illustrates the relationship between COVID-19 symptoms and the exhaled viral levels at the individual level using data from samples collected with this invention.
Figure 11B:
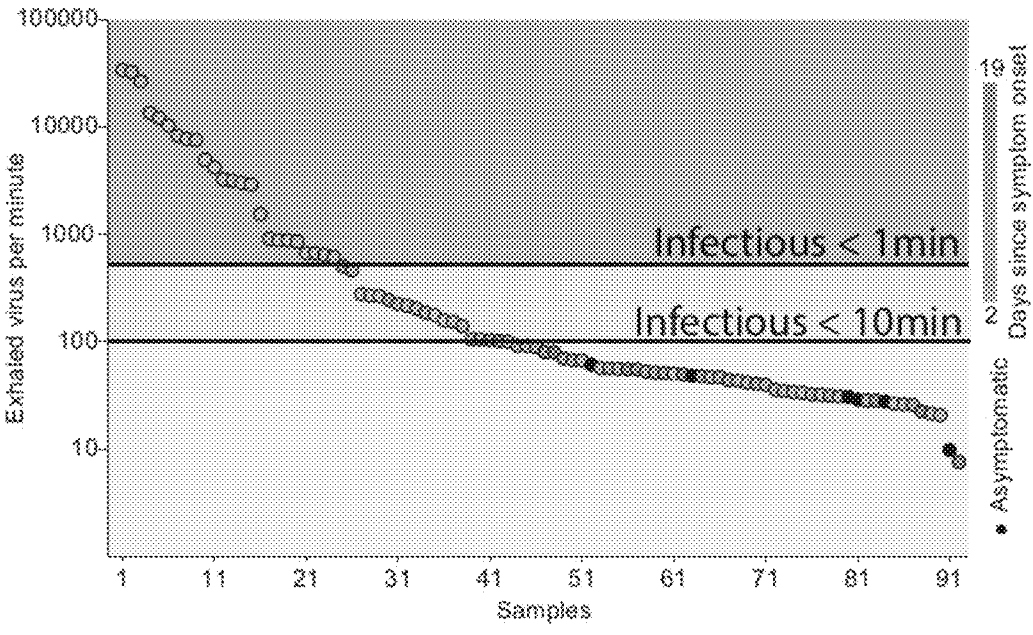
FIG. 11B illustrates the relationship between the exhaled viral levels at the individual level and the timing of sample collection relative to infection onset using data from samples collected with this invention.

FIG. 11A-B illustrate the relationship between exhaled virus and symptom duration and severity.

For each sample collected, any current symptoms are noted and if present, their timing relative to onset of infection. Samples were grouped according to the severity of symptoms during the breathing session, and levels plotted of virus in each sample for each group. FIG. 11A reflects a statistically significant relationship between symptom severity and levels of virus being exhaled. However, notably and importantly, this relationship was not perfect. Some individuals with very few symptoms were exhaling large amounts of virus, and some individuals with severe symptoms exhaled lower levels of virus. This suggests that determination of exhaled viral levels at the individual level is critical for assessment of infectiousness of a given patient. FIG. 11B then arranges samples along a sorted axis according to how much virus they contained, and color-coded each data point according to the timing of sample collection relative to infection onset. This reveals that the samples collected early in the course of infection generally contained more virus, though again, this relationship was not perfect, and some individuals exhaled large amounts of virus late in the course of their infection.

Example 5

Figure 12A:
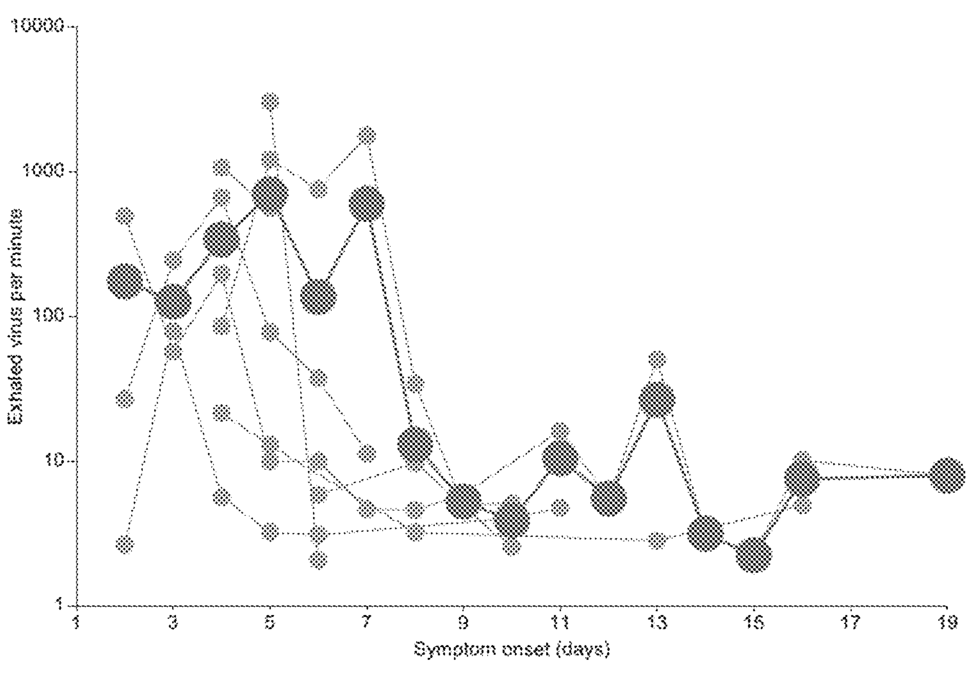
FIG. 12A-B illustrates individual exhaled levels of virus over the course of infection using data from samples collected with this invention.
Figure 12B:
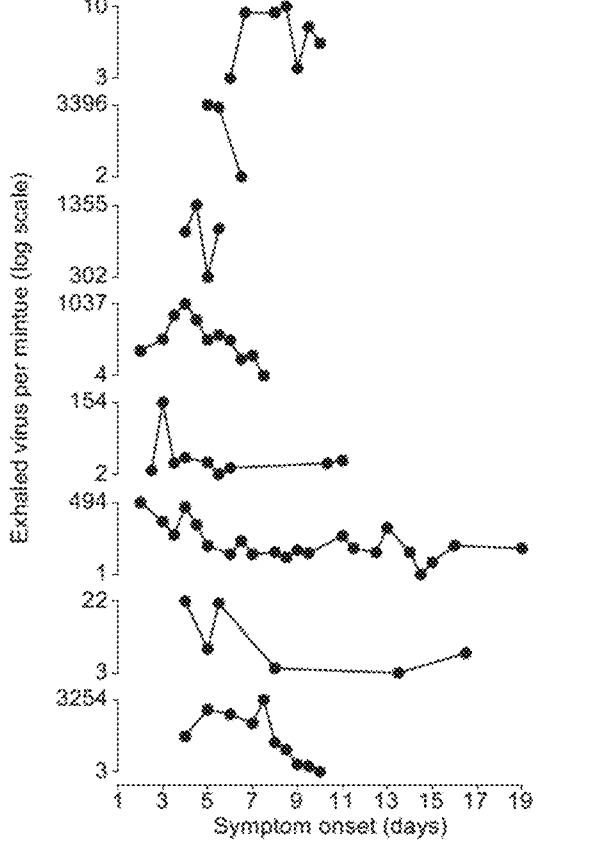

FIG. 12A-B illustrate individual exhaled levels of virus over the course of infection.

Given the significant individual variability in levels of exhaled virus, the present invention next aimed to characterize how levels of viral shedding on breath change over the course of infection, at the individual level. To do this, 8 patients were recruited to collect samples twice daily over a number of days (ranging from 2 to 14, depending on the patients' availability). Varying levels of exhaled virus are found over the course of infection for individual patients, though most patients showed maximal exhaled virus at around day 3 or 4 post-symptom-onset, as reflected in FIG. 12A.

These results indicate that patients can easily perform this task at home, multiple times a day, for days at a time, with very little instruction, and that the course of infectiousness is variable across individual patients, as reflected in FIG. 12B.

These results also indicate that given that respiratory pathogens are spread through exhaled aerosols and droplets across a wide range of diseases including viral, bacterial and fungal respiratory diseases, using any standard method for detecting and quantifying respiratory pathogens, this methodology is appropriate for detection and quantification of infectiousness of any respiratory pathogen which is transmitted through exhaled breath.

The foregoing description of the exemplary embodiments of the invention has been presented only for the purposes of illustration and description and is not intended to be exhaustive or to limit the invention to the precise forms disclosed. Many modifications and variations are possible in light of the above teaching.

The embodiments were chosen and described in order to explain the principles of the invention and their practical application so as to enable others skilled in the art to utilize the invention and various embodiments and with various modifications as are suited to the particular use contemplated. Alternative embodiments will become apparent to those skilled in the art to which the present invention pertains without departing from its spirit and scope. Accordingly, the scope of the present invention is defined by the appended claims rather than the foregoing description and the exemplary embodiments described therein.

Some references, which may include patents, patent applications and various publications, are cited and discussed in the description of this invention. The citation and/or discussion of such references is provided merely to clarify the description of the present invention and is not an admission that any such reference is "prior art" to the invention described herein. All references cited and discussed in this specification are incorporated herein by reference in their entireties and to the same extent as if each reference was individually incorporated by reference.

What is claimed is:

1. A device for collecting exhaled breath condensate of a subject, comprising:
- a sample tube having a first end for receiving exhaled breath and a second end for exhaled breath to exit;
- a cooling sleeve for cooling the sample tube;
- a mouthpiece or nose mask adapted to communicate with the first end of the sample tube for directing exhaled breath into the sample tube; and
- a plunger to be inserted into the sample tube via the first end of the sample tube,
  - wherein the plunger and the sample tube form an airtight connection such that when the plunger is pushed into the sample tube, the exhaled breath condensate inside the sample tube is removed from the sample tube via the second end of the sample tube.

2. The device of claim 1, wherein
- the mouthpiece or nose mask are arranged in a straight line with respect to the sample tube in order to produce breath flow into the tube along an essentially non-angular path.

3. The device of claim 1, wherein
- the second end of the sample tube has an aperture whose diameter is narrower than a diameter of the sample tube so as to create resistance to exhaled breath flowing in the sample tube.

4. The device of claim 3, wherein
- the diameter of the aperture is ¼ of the diameter of the sample tube.

5. The device of claim 1, wherein the device further comprises:
- a one-way valve placed between the mouthpiece or the nose mask and the sample tube.

6. The device of claim 1, wherein the device further comprises:
- an insulator placed outside of the cooling sleeve so as to thermally insulate the cooling sleeve from surrounding environment.

7. The device of claim 1, wherein the plunger comprises a plunger body, a seal end, a tapered neck, and a thumb rest.

8. The device of claim 5, wherein the one-way valve is used as the plunger.

* * * * *